(12) United States Patent
Meng et al.

(10) Patent No.: US 8,927,562 B2
(45) Date of Patent: Jan. 6, 2015

(54) FUSED TRICYCLIC INHIBITORS OF MAMMALIAN TARGET OF RAPAMYCIN

(75) Inventors: Zhaoyang Meng, Lansdale, PA (US); Panduranga Adulla Reddy, Walpole, MA (US); M. Arshad Siddiqui, Newton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/876,192

(22) PCT Filed: Sep. 26, 2011

(86) PCT No.: PCT/US2011/053201
§ 371 (c)(1),
(2), (4) Date: Mar. 27, 2013

(87) PCT Pub. No.: WO2012/047570
PCT Pub. Date: Apr. 12, 2012

(65) Prior Publication Data
US 2013/0281474 A1    Oct. 24, 2013

Related U.S. Application Data

(60) Provisional application No. 61/387,207, filed on Sep. 28, 2010.

(51) Int. Cl.
*A61K 31/519* (2006.01)
*C07D 487/14* (2006.01)
*C07D 495/14* (2006.01)
*C07D 487/04* (2006.01)

(52) U.S. Cl.
CPC ............. *C07D 495/14* (2013.01); *A61K 31/519* (2013.01); *C07D 487/04* (2013.01); *C07D 487/14* (2013.01)
USPC .......................................... 514/267; 544/251

(58) Field of Classification Search
CPC ........................... A61K 31/519; C07D 487/14
USPC .......................................... 514/267; 544/251
See application file for complete search history.

(56) References Cited

U.S. PATENT DOCUMENTS

| | | |
|---|---|---|
| 2004/0072833 A1 | 4/2004 | Nakai et al. |
| 2007/0027156 A1 | 2/2007 | Nakai et al. |
| 2007/0173519 A1 | 7/2007 | Unoki et al. |

FOREIGN PATENT DOCUMENTS

WO    WO 2006/098519    *    9/2006    ............ C07D 487/14

* cited by examiner

*Primary Examiner* — Erich A Leeser
(74) *Attorney, Agent, or Firm* — Richard S. Parr; Laura M. Ginkel

(57) ABSTRACT

This invention relates to novel fused tricyclic compounds that are inhibitors of mammalian Target of Rapamycin (mTOR) kinase, which is also known as FRAP, RAFT, RAPT or SEP, and are useful in the treatment of cellular proliferative diseases, for example cancer and other proliferative disorders.

8 Claims, No Drawings

FUSED TRICYCLIC INHIBITORS OF MAMMALIAN TARGET OF RAPAMYCIN

REFERENCE TO SEQUENCE LISTING SUBMITTED ELECTRONICALLY

The sequence listing of the present application is being submitted electronically via EFS-Web as an ASCII formatted sequence listing with a file name "MRLONC00050USPCT-SEQTXT-27JUNE2013.txt", creation date of Jun. 27, 2013 and a size of 878 bytes. This sequence listing submitted via EFS-Web is part of the specification and is herein incorporated by reference in its entirety.

BACKGROUND OF THE INVENTION

This invention relates to novel fused tricyclic compounds that are inhibitors of mammalian Target of Rapamycin (mTOR) kinase, which is also known as FRAP, RAFT, RAPT or SEP, and are useful in the treatment of cellular proliferative diseases, for example cancer and other proliferative disorders.

The mammalian target of rapamycin (mTOR) is a central regulator of cell growth and proliferation and plays a gatekeeper role in the control of cell cycle progression. mTOR mediates mitgenic signals from P13K/AKT through to the downstream targets S6K1 and 4E-BP1 and to Ser 473 on AKT. Recently, it has been shown that mTOR exists in two complexes. Rator-mTOR complex (mTORC1) is a rapamycin-sensitive complex that phosphorylates S6K1 (ribosomal S6 kinase 1) and 4E-BP1 (eukaryotic translation initiation factor 4E-binding protein). Rictor-mTOR complex (mTORC2) is a rapamycin-insensitive complex that phosphorlates AKT. Although the precise mechanism by which rapamycin inhibitis mTOR function is not well understood, rapamycin partially inhibits mTOR function through mTORC1. Since mTORC2 is involved in the regulation of cell survival and actin cytoskeletal organization in a rapamycin-independent manner, complete inhibition of mTOR function through inhibition of both mTORC1 and mTORC2 may lead to a broader spectrum antitumor activity and/or better efficacy than through inhibition of mTORC1 alone.

There exists a need in the art for small-molecule compounds having desirable physiochemical properties that are useful for treating cancer and other proliferative disorders. Specifically, there exists a need for small molecule inhibitors of mTOR kinase that block signaling through mTORC1 and mTORC2 for treating cancer and other cell proliferative diseases.

SUMMARY OF THE INVENTION

The present invention relates to novel fused tricyclic derivatives, that are useful for treating cancer and other cellular proliferative diseases, for treating disorders associated with mTOR activity, and for inhibiting the mTOR kinase. The compounds of the invention may be illustrated by the Formula I:

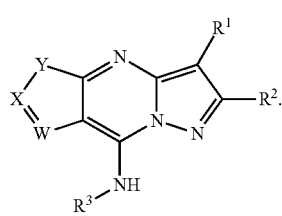

I

DETAILED DESCRIPTION OF THE INVENTION

The compounds of this invention are useful in the inhibition of mTOR kinase, and are illustrated by a compound of the formula:

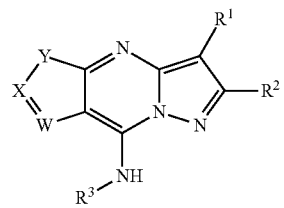

wherein the dotted line between W and X represents an optional double bond;
W is $CR^xR^y$, $NR^5$, or $SO_m$;
X is $CR^xR^y$, $NR^6$, or $SO_m$;
Y is $CR^xR^y$, $CR^xNHR^5$, $NR^5$, O, C(O) or $SO_m$;
$R^1$ is hydrogen, halo, —$C(O)R^5$, $C_{1-6}$ alkyl, $C_{2-6}$ alkenyl, $C_{2-6}$ alkynyl, $C_{3-4}$ cycloalkyl, $C_{3-8}$ cycloalkenyl, aryl, heteroaryl or heterocyclyl, wherein said alkyl, alkenyl, alkynyl, cycloalkyl, cycloalkenyl, aryl, heteroaryl and heterocyclyl groups are optionally substituted with one to three substituents independently selected from the group consisting of $R^4$, halo, cyano, $C_{1-6}$ alkyl, $C_{1-6}$ haloalkyl, $(CR^yR^z)_mOR^y$, $(CR^yR^z)_mNR^yR^z$, $C(O)R^y$, $C(O)OR^y$, $SO_mR^y$, $C(O)NR^yR^z$, $NR^yC(O)R^3$ and $NHR^4$;
$R^2$ is hydrogen, halo, cyano, $NR^yR^z$, $OR^y$, $C_{1-6}$ alkyl or $C_{1-6}$ haloalkyl;
$R^3$ is hydrogen, $NR^yR^z$, $(CR^yR^z)_mOR^y$, $C_{1-6}$ alkyl, $C_{2-6}$ alkenyl, $C_{2-6}$ alkynyl, $C_{3-8}$ cycloalkyl, $C_{3-8}$ cycloalkenyl, aryl, heteroaryl or heterocyclyl, wherein said cycloalkyl, cycloalkenyl, aryl, heteroaryl and heterocyclyl groups are optionally substituted with one to three substituents independently selected from the group consisting of halo, cyano, $C_{1-6}$ alkyl, $C_{1-6}$ haloalkyl and $OR^y$;
$R^4$ is $C_{3-8}$ cycloalkyl, $C_{3-8}$ cycloalkenyl, aryl, heteroaryl or heterocyclyl, wherein said cycloalkyl, cycloalkenyl, aryl, heteroaryl and heterocyclyl groups are optionally substituted with one to three substituents independently selected from the group consisting of halo, cyano, $C_{1-6}$ alkyl, $C_{1-6}$ haloalkyl, $(CR^yR^z)_mOR^y$, $O(C_{1-6}$ haloalkyl), $C(O)R^y$, $C(O)OR^y$, $SO_mR^y$ and $NR^yR^z$;
$R^5$ is not present, hydrogen, aryl, heteroaryl, heterocyclyl or heterocyclyl($R^6$);
$R^6$ is not present, (C=O)$C_{1-6}$ alkyl, (C=O)aryl, (C=O)heteroaryl, (C=O)O($C_{1-6}$ alkyl)-$R^4$, wherein said alkyl and heteroaryl groups are optionally substituted with one to three substituents independently selected from the group consisting of halo, hydroxyl and $NR^yR^4$;
$R^x$ is hydrogen or $C_{1-6}$ alkyl;
$R^y$ is not present, hydrogen, $C_{1-6}$ alkyl or $C_{1-6}$ haloalkyl, wherein said alkyl group is optionally substituted with one to three hydroxyl;
$R^z$ is hydrogen, $C_{1-6}$ alkyl or $C_{1-6}$ haloalkyl, wherein said alkyl group is optionally substituted with one to three hydroxyl;
m is an integer from zero to two;
or a pharmaceutically acceptable salt thereof. X is $CR^xR^y$, $NR^6$ or $SO_m$; Y is $CR^xR^y$, $CR^xNHR^5$ or $NR^5$;

In a class of the invention, W is $CR^xR^y$.

In a class of the invention, X is $CR^xR^y$, $NR^6$ or $SO_m$. In a subclass of the invention, X is $CR^xR^y$. In a subclass of the invention, X is $NR^6$. In a subclass of the invention, X is $SO_m$.

In a class of the invention, Y is $CR^xR^y$, $CR^xNHR^5$ or $NR^5$. In a subclass of the invention, Y is $CR^xR^y$. In a subclass of the invention, Y is $CR^xNHR^5$. In a subclass of the invention, Y is $NR^5$ In a class of the invention, $R^1$ is heteroaryl, wherein said heteroaryl group is optionally substituted with one to three substituents independently selected from the group consisting of $R^4$, halo, cyano, $C_{1-6}$ alkyl, $C_{1-6}$ haloalkyl, $(CR^yR^z)_m$ $OR^y$, $(CR^yR^z)_m NR^yR^z$, $OR^y$, $C(O)R^y$, $C(O)OR^y$, $SO_mR^y$, $C(O)NR^yR^z$ and $NR^yR^z$. In a subclass of the invention, $R^1$ is heteroaryl, wherein said heteroaryl group is optionally substituted with one to three substituents independently selected from the group consisting of $R^4$, halo, and $C_{1-6}$ alkyl. In a subclass of the invention, $R^1$ is pyridinyl or quinolinyl wherein said pyridinyl and quinolinyl groups are optionally substituted with one to three substituents independently selected from the group consisting of $R^4$, halo, $C_{1-6}$ alkyl and $OR^y$. In a subclass of the invention, $R^1$ is pyridinyl which is substituted with phenyl. In a subclass of the invention, $R^1$ is pyridinyl which is substituted with pyrazolyl, pyrrolyl, thiazolyl, thiophenyl, pyridinyl or pyrazinyl, wherein said pyrazolyl, pyrrolyl, thiazolyl, thiophenyl, pyridinyl or pyrazinyl groups are optionally substituted with one to three substituents independently selected from the group consisting of halo and $C_{1-6}$ alkyl. In a subclass of the invention, $R^1$ is pyrazolyl which is optionally substituted with one to three substituents independently selected from the group consisting of $R^4$, halo, $C_{1-6}$ alkyl and $OR^y$. In a subclass of the invention, $R^1$ is quinolinyl, which is optionally substituted with one to three substituents independently selected from the group consisting of halo, $OR^y$ and $C_{1-6}$ alkyl. In a subclass of the invention, $R^1$ is quinolinyl, which is optionally substituted with halo.

In a class of the invention, $R^4$ is aryl or heteroaryl, wherein said heteroaryl group is optionally substituted with $C_{1-6}$ alkyl.

In a class of the invention, $R^5$ is hydrogen, heterocyclyl or heterocyclyl($R^6$).

Specific examples of the compounds of the instant invention include, but are not limited to:

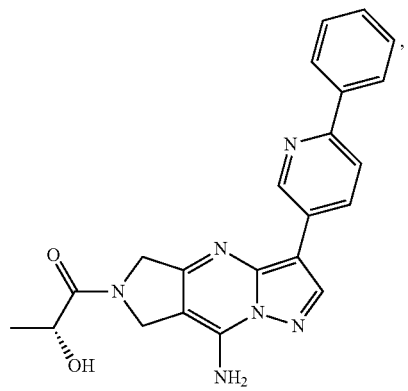

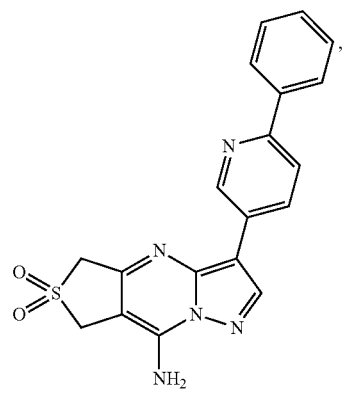

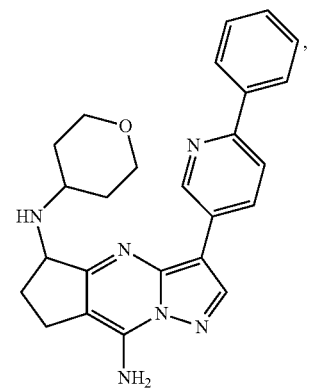

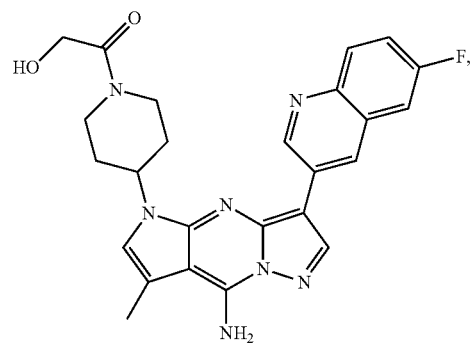

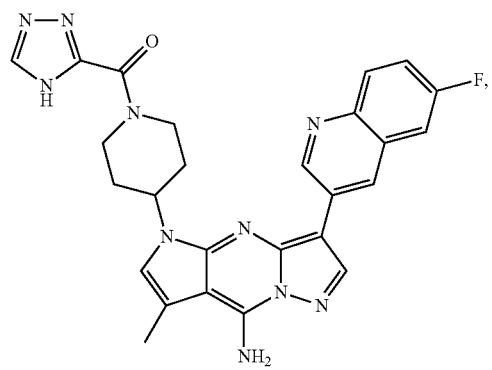

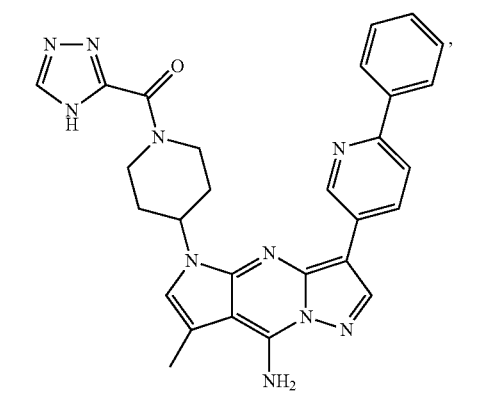
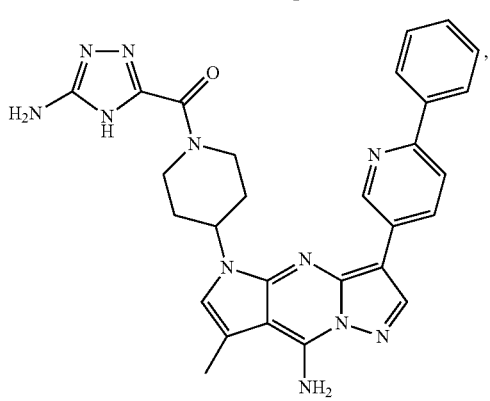
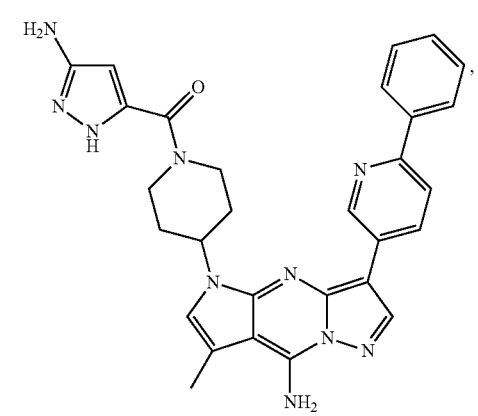
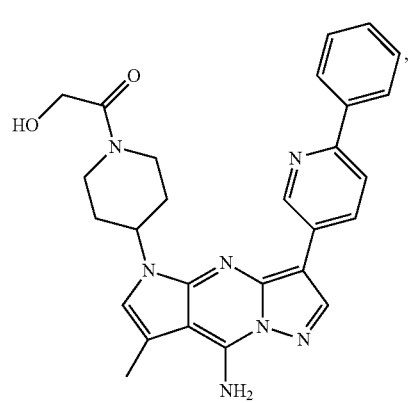
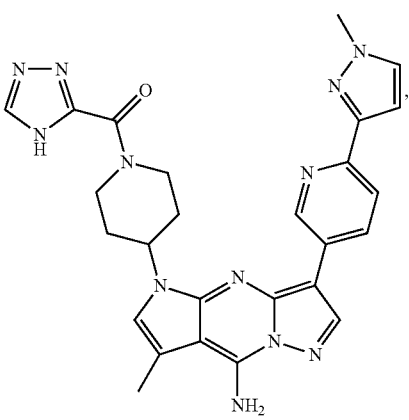
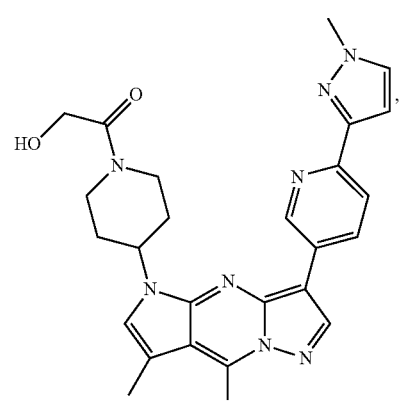
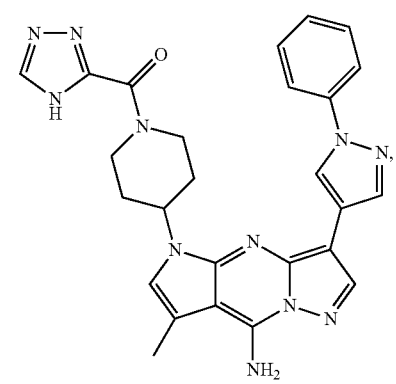
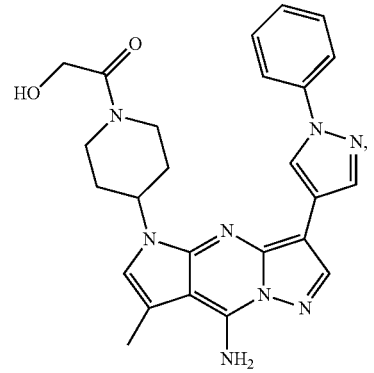

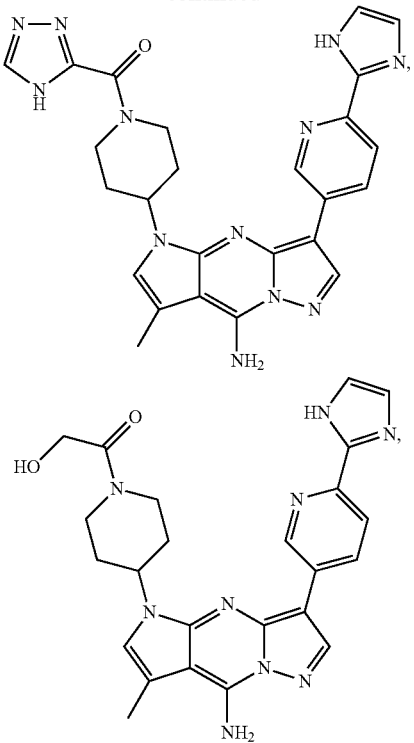

or a pharmaceutically acceptable salt or stereoisomer thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain, therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

When any variable (e.g. $R^6$) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases another embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "haloalkyl" means an alkyl radical as defined above, unless otherwise specified, that is substituted with one to five, preferably one to three halogen. Representative examples include, but are not limited to trifluoromethyl, dichloroethyl, and the like.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "alkynyl" refers to a hydrocarbon radical straight or branched, containing from 2 to 10 carbon atoms, unless otherwise specified, containing at least 1 carbon to carbon triple bond. Up to 3 carbon-carbon triple bonds may be present. Thus, "$C_2$-$C_6$ alkynyl" means an alkynyl radical having from 2 to 6 carbon atoms. Alkynyl groups include ethynyl, propynyl and butynyl. As described above with respect to alkyl, the straight, branched or cyclic portion of the alkynyl group may contain triple bonds and may be substituted if a substituted alkynyl group is indicated.

In certain instances, substituents may be defined with a range of carbons that includes zero, such as $(C_0-C_6)$alkylenearyl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

The term "heteroaryl," as used herein, represents a stable monocyclic or bicycle ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. For the purposes of this invention, the term "heterocyclic" is also considered to be synonymous with the terms "heterocycle" and "heterocyclyl" and is understood as also having the definitions set forth herein. "Heterocyclyl" therefore includes the above mentioned heteroaryls, as well as dihydro and tetrahydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro, fluoro, bromo and iodo.

The alkyl, alkenyl, alkynyl, cycloalkyl, aryl, heteroaryl and heterocyclyl substituents may be substituted or unsubstituted, unless specifically defined otherwise. For example, a $(C_1-C_6)$ alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: —$C(=O)CH_2CH(OH)CH_3$, —$(C=O)OH$, —$CH_2(OH)CH_2CH(O)$, and so on.

Included in the instant invention is the free form of compounds of the instant invention, as well as the pharmaceutically acceptable salts and stereoisomers thereof. The term "free form" refers to the amine compounds in non-salt form. The encompassed pharmaceutically acceptable salts not only include the salts exemplified for the specific compounds described herein, but also all the typical pharmaceutically acceptable salts of the free form of compounds of the instant invention. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. When the compound of the present invention is acidic, the term "free form" refers to the compound in its non-salt form, such that the acidic functionality is still protonated.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

It will also be noted that the compounds of the present invention may potentially be internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom. An isolated compound having internally balance charges, and thus not associated with a intermolecular counterion, may also be considered the "free form" of a compound.

Utilities

The compounds of the invention are useful to bind to and/or modulate the activity of mTOR kinase. In an embodiment, the compounds of the instant invention inhibit the activity of mTORC1. In another embodiment, the compounds of the instant invention inhibit the activity of mTORC2. In another embodiment, the compounds of the instant invention inhibit the activity of both mTORC1 and mTORC2. In this context, modulate means either increasing or decreasing kinase activity of mTOR. In an embodiment, the compounds of the instant invention inhibit the kinase activity of mTOR.

The compounds of the invention find use in a variety of applications. As will be appreciated by those skilled in the art, the kinase activity of mTOR may be modulated in a variety of ways; that is, one can affect the phosphorylation/activation of mTOR either by modulating the initial phosphorylation of the protein or by modulating the autophosphorylation of the other active sites of the protein. Alternatively, the kinase activity of mTOR may be modulated by affecting the binding of a substrate of mTOR phosphorylation.

The compounds of the invention are used to treat or prevent cellular proliferation diseases. Disease states which can be treated by the methods and compositions provided herein include, but are not limited to, cancer (further discussed below), autoimmune disease, viral disease, fungal disease, neurological/neurodegenerative disorders, arthritis, inflammation, anti-proliferative (e.g. ocular retinopathy), neuronal, alopecia, cardiovascular disease, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. Thus, in one embodiment, the invention herein includes application to cells or individuals which are afflicted or may eventually become afflicted with any one of these disorders or states.

The compounds, compositions and methods provided herein are particularly deemed useful for the treatment and prevention of cancer including solid tumors such as skin, breast, brain, cervical carcinomas, testicular carcinomas, etc. In an embodiment, the instant compounds are useful for treating cancer. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia,), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions. In an embodiment of the invention, cancers that may be treated by the compounds, compositions and methods of the invention include, in addition to the cancers listed above: Lung: bronchogenic carcinoma (non-small cell lung); Gastrointestinal: rectal, colorectal and colon; Genitourinary tract: kidney (papillary renal cell carcinoma); and Skin: head and neck squamous cell carcinoma.

In another embodiment, the compounds of the instant invention are useful for treating or preventing cancer selected from: head and neck squamous cell carcinomas, histiocytic lymphoma, lung adenocarcinoma, small cell lung cancer, non-small cell lung cancer, pancreatic cancer, papillary renal cell carcinoma, liver cancer, gastric cancer, colon cancer, multiple myeloma, glioblastomas and breast carcinoma. In yet another embodiment, the compounds of the instant invention are useful for treating or preventing cancer selected from: histiocytic lymphoma, lung adenocarcinoma, small cell lung cancer, pancreatic cancer, liver cancer, gastric cancer, colon cancer, multiple myeloma, glioblastomas and breast carcinoma. In still another embodiment, the compounds of the instant invention are useful for treating cancer selected from: histiocytic lymphoma, lung adenocarcinoma, small cell lung cancers, pancreatic cancer, liver cancer, gastric cancer, colon cancer, multiple myeloma, glioblastomas and breast carcinoma.

In another embodiment, the compounds of the instant invention are useful for the prevention or modulation of the metastases of cancer cells and cancer. In particular, the compounds of the instant invention are useful to prevent or modulate the metastases of ovarian cancer, childhood hepatocellular carcinoma, metastatic head and neck squamous cell carcinomas, gastric cancers, breast cancer, colorectal cancer, cervical cancer, lung cancer, nasopharyngeal cancer, pancreatic cancer, glioblastoma and sarcomas.

The compounds of this invention may be administered to mammals, preferably humans, either alone or in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a fowl suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solution. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

In a further example, compounds of the instant invention can be administered in a total daily dose of up to 1000 mg. Compounds of the instant invention can be administered once daily (QD), or divided into multiple daily doses such as twice daily (BID), and three times daily (TID). Compounds of the instant invention can be administered at a total daily dosage of up to 1000 mg, e.g., 200 mg, 300 mg, 400 mg, 600 mg, 800 mg or 1000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholine-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, SAHA, TSA, oxamflatin, PXD101, MG98, valproic acid and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-

2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

Specific anti-IGF-1R antibodies include, but are not limited to, dalotuzumab, figitumumab, cixutumumab, SHC 717454, Roche R1507, EM164 or Amgen AMG479.

The mTOR inhibitors in current clinical development are structural analogs of rapamycin. The mTOR inhibitors of the instant invention include ridaforolimus, temsirolimus, everolimus, a rapamycin-analog and combinations thereof.

Ridaforolimus, also known as AP 23573, MK-8669 and deforolimus, is a unique, non-prodrug analog of rapmycin that has antiproliferative activity in a broad range of human tumor cell lines in vitro and in murine tumor xenograft models utilizing human tumor cell lines. Ridaforolimus has been administered to patients with advanced cancer and is currently in clinical development for various advanced malignancies, including studies in patients with advanced soft tissue or bone sarcomas. Thus far, these trials have demonstrated that ridaforolimus is generally well-tolerated with a predictable and manageable adverse even profile, and possess anti-tumor activity in a broad range of cancers. A description and preparation of ridaforolimus is described in U.S. Pat. No. 7,091,213 to Ariad Gene Therapeutics, Inc., which is hereby incorporated by reference in its entirety.

Temsirolimus, also known as Torisel®, is currently marketed for the treatment of renal cell carcinoma. A description and preparation of temsirolimus is described in U.S. Pat. No. 5,362,718 to American Home Products Corporation, which is hereby incorporated by reference in its entirety.

Everolimus, also known as Certican® or RAD001, marketed by Novartis, has greater stability and enhanced solubility in organic solvents, as well as more favorable pharmokinetics with fewer side effects than rapamycin (sirolimus). Everolimus has been used in conjunction with microemulsion cyclosporin (Neoral®, Novartis) to increase the efficacy of the immunosuppressive regime.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)-phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet* 61:785-789, 1997) and Kufe et al (*Cancer Medicine*, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8)1105-13), and interferon gamma (*J Immunol* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); didemnin B; 17-DMAG; docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); ethinyl estradiol; etoposide phosphate (Etopophos®); etoposide, VP-16 (Vepeside); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane 1123 injection (AdreView); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek®); raloxifene hydrochloride (Evista®); Rituximab (Rituxan®); romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston®); Tositumomab (Bexxar®); Tositumomab/I-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

Thus, the scope of the instant invention encompasses the use of the instantly claimed compounds in combination with a second compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an apoptosis inducing agent, a bisphosphonate, an aromatase inhibitor, an siRNA therapeutic γ-secretase inhibitors, agents that interfere with receptor tyrosine kinases (RTKs), an agent that interferes with a cell cycle checkpoint and any of the therapeutic agents listed above.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-$\alpha$, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-$\gamma$ agonist, a PPAR-$\delta$ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an apoptosis inducing agent, a bisphosphonate, an aromatase inhibitor, an siRNA therapeutic and an agent that interferes with a cell cycle checkpoint.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-$\gamma$ agonist, a PPAR-$\epsilon$ agonist; an inhibitor of cell proliferation and survival signaling, a bisphosphonate, an aromatase inhibitor, an siRNA therapeutic and an agent that interferes with a cell cycle checkpoint.

Further included within the scope of the invention is a method of treating or preventing a disease in which angiogenesis is implicated, which is comprised of administering to a mammal in need of such treatment a therapeutically effective amount of a compound of the present invention. Other inhibitors of MET may also be administered for this method of treatment. Ocular neovascular diseases, which may result in certain forms of blindness, are examples of conditions where much of the resulting tissue damage can be attributed to aberrant infiltration of blood vessels in the eye. The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Routes of systemic administration of the compounds of the present invention described above may be utilized in the treatment of such ocular neovascular diseases. Other routes of ocular administration may also be employed, such as topical, periocular, intravitreal and the like. Intravitreal implants coated with a drug:polymer matrix may also be employed.

Ophthalmic pharmaceutical compositions that are adapted for topical administration to the eye may be in the form of solutions, suspensions, ointments, creams or as a solid insert. Ophthalmic formulations of this compound may contain from 0.01 ppm to 1% and especially 0.1 ppm to 1% of medicament. For a single dose, from between 0.01 to 5000 ng, preferably 0.1 to 500 ng, and especially 1 to 100 ng of the compound can be applied to the human eye. Formulations useful for intravitreal administration are similar to saline solutions described previously for intravenous administration.

These and other aspects of the invention will be apparent from the teachings contained herein.

SCHEMES AND EXAMPLES

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention hereinabove.

Examples provided are intended to assist in a further understanding of the invention. Particular materials employed, species and conditions are intended to be illustrative of the invention and not limiting of the reasonable scope thereof.

The abbreviations used herein have the following tabulated meanings. Abbreviations not tabulated below have their meanings as commonly used unless specifically stated otherwise.

| | |
|---|---|
| Ac = | acetyl |
| ACN = | acetonitrile |
| Bn = | benzyl |
| BPIN = | bis(pinacolato)diboron |
| CAMP = | cyclic adenosine-3',5'-monophosphate |
| CAN = | ceric ammonium nitrate |
| DAST = | N,N-Diethylaminosulfur trifluoride |
| DMA = | N,N-dimethylacetamide |
| DIEA = | N,N-Diisopropylethylamine |
| DBU = | 1,8-diazabicyclo[5.4.0]undec-7-ene |
| DCM = | dichloromethane |
| DIAD = | diisopropyl azodicarboxylate |
| DIBAL = | diisobutylaluminum hydride |
| DIPEA = | N,N-Diisopropylethylamine |
| DMAP = | 4-(dimethylamino)pyridine |
| DME = | dimethoxyethane |
| DMF = | N,N-dimethylformamide |
| DMFDMA = | dimethylformamide dimethyl acetal |
| DPPA = | diphenylphosphoryl azide |
| EDC = | 3-(ethyliminomethyleneamino)-N,N-dimethyl-propan-1-amine |
| EDCl = | dichloroethane |
| $Et_3N$ = | triethylamine |
| EtOAc = | ethyl acetate |
| GST = | glutathione transferase |
| HCl = | hydrochloric acid |
| HMDS = | hexamethyldisilazide |
| HOBt = | 1-hydroxybenzotriazole |
| hr = | hour |
| KOAc = | Potassium acetate |
| $K_3PO_4$ = | Potassium phosphate |
| LDA = | lithium diisopropylamide |
| mCPBA = | metachloroperbenzoic acid |
| MMPP = | monoperoxyphthalic acid |
| MPPM = | monoperoxyphthalic acid, magnesium salt $6H_2O$ |
| $MnO_2$ = | manganese dioxide |
| MPLC = | medium pressure liquid chromatography |
| Ms = | methanesulfonyl = mesyl = $SO_2Me$ |
| MsO = | methanesulfonate = mesylate |
| μW = | microwave |
| NaH = | sodium hydride |
| $Na_2CO_3$ = | Sodium bicarbonate |
| NaOEt = | sodium ethoxide |
| NBS = | N-bromosuccinimide |
| NIS = | N-Iodosuccinimide |
| NMP = | N-Methyl-2-pyrrolidone |
| NSAID = | non-steroidal anti-inflammatory drug |
| $NH_4OH$ = | Ammonium hydroxide |
| o-Tol = | ortho-tolyl |
| OXONE ® = | $2KHSO_5 \cdot KHSO_4 \cdot K_2SO_4$ |
| PCC = | pyridinium chlorochromate |
| PDC = | pyridinium dichromate |
| PDE = | phosphodiesterase |
| $Pd(PPh_3)_4$ = | tetrakis(triphenylphosphine)palladium |
| $PdCl_2(dppf)_2$ = | 1,1'-Bis(diphenylphosphino)ferrocene-palladium(II)dichloride |
| Ph = | phenyl |
| Phe = | benzenediyl |
| $PhNTf_2$ = | N-phenyl bis-trifluoromethanesulfonimide |
| PMB = | para-methoxybenzyl |
| $POCl_3$ = | phosphoryl chloride |
| PPA = | polyphosphoric acid |
| Pye = | pyridinediyl |
| r.t. = | room temperature |
| Rac. = | racemic |
| SAM = | aminosulfonyl or sulfonamide or $SO_2NH_2$ |
| SEM = | 2-(trimethylsilyl)ethoxymethoxy |
| SPA = | scintillation proximity assay |
| TBAF = | tetra-n-butylammonium fluoride |
| TBTU = | O-(benzotriazol-1-yl)-N,N,N',N'-tetramethyluronium tetrafluoroborate |
| TEA = | triethylamine |
| Th = | 2- or 3-thienyl |
| THP = | tetrahydropyran |
| TFA = | trifluoroacetic acid |
| TFAA = | trifluoroacetic acid anhydride |
| THF = | tetrahydrofuran |
| Thi = | thiophenediyl |
| TLC = | thin layer chromatography |
| TMS—CN = | trimethylsilyl cyanide |
| TMSI | trimethylsilyl iodide |
| Tz = | 1H (or 2H)-tetrazol-5-yl |
| XPhos = | 2-dicyclohexylphosphino-2',4',6'-triisopropylbiphenyl |
| $C_3H_5$ = | allyl |

Alkyl Group Abbreviations

| | |
|---|---|
| Me = | methyl |
| Et = | ethyl |
| n-Pr = | normal propyl |
| i-Pr = | isopropyl |
| n-Bu = | normal butyl |

| | |
|---|---|
| i-Bu = | isobutyl |
| s-Bu = | secondary butyl |
| t-Bu = | tertiary butyl |
| c-Pr = | cyclopropyl |
| c-Bu = | Cyclobutyl |
| c-Pen = | cyclopentyl |
| c-Hex = | cyelohexyl |

General Scheme 1

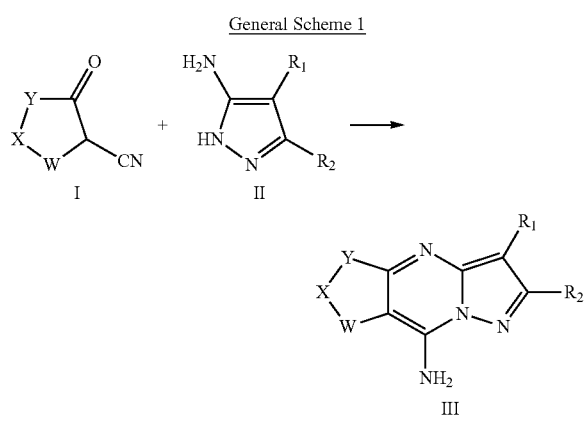

A mixture of β-keto nitrile I and substituted 3-amino pyrazole II is heated neat or in appropriate solvent such as toluene, HOAc to afford the tricyclic compound III (General Scheme 1).

General Scheme 2

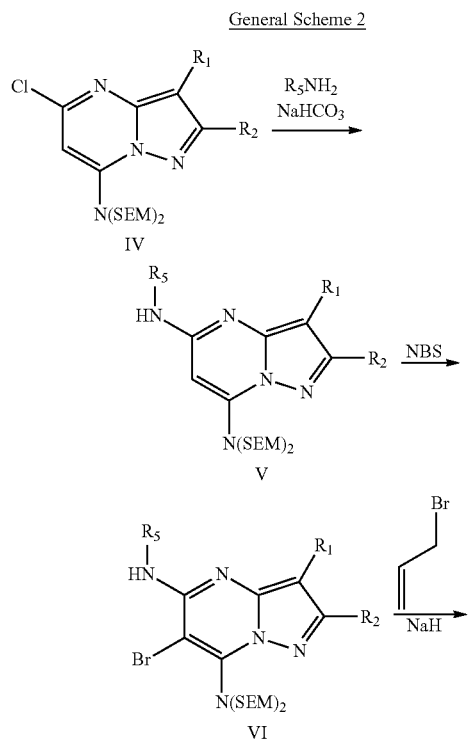

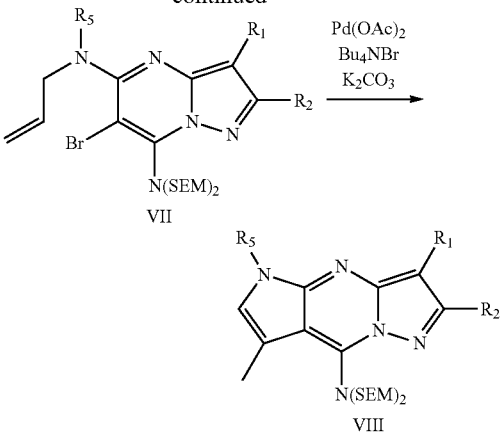

Substituted pyrazolo[1,5-a]pyrimidine IV is treated with amine $R_5NH_2$ and an appropriate base such as $NaHCO_3$ in an appropriate solvent such as NMP to provide the corresponding displacement intermediate V (General Scheme 2). Intermediate V is brominated by reacting with N-Bromosuccinimide (NBS) in an appropriate solvent or solvent mixture such as DCM, DCM-$CH_3CN$ and DMF to provide the corresponding bromide intermediate VI. Bromide intermediate VI is treated with allyl bromide and an appropriate base such as NaH in an appropriate solvent or solvent mixture such DMF to afford the corresponding intermediate VII. Intermediate VII is treated with an appropriate base, such as $K_2CO_3$, in the presence of an appropriate catalyst, such as $Pd(OAc)_2$, in an appropriate solvent, such as DMF, to afford intermediate VIII.

Example 1

Preparation of (R)-1-(8-amino-3-(6-phenylpyridin-3-yl)-5H-pyrazolo[1,5-a]pyrrolo[3,4-d]pyrimidin-6(7H)-yl)-2-hydroxypropan-1-one Step 1: Preparation of 2-(6-phenylpyridin-3-yl)acetonitrile

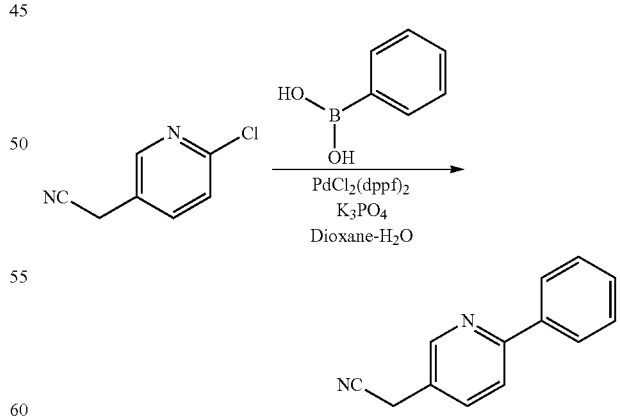

Phenylboronic acid (4630.9 mg, 37.98 mmol), $K_3PO_4$ (20129 mg, 94.95 mmol), and $PdCl_2(dppf)\cdot CH_2Cl_2$ (1291 mg, 1.58 mmol) was added to a solution of 2-(6-chloropyridin-3-yl)acetonitrile (5000 mg, 31.65 mmol) in dioxane (100 mL) and $H_2O$ (10 mL). The resulting mixture was stirred at 75° C. under argon overnight. The mixture was diluted with H₂O and then extracted with ethyl acetate (×2). The combined organic layers were washed with brine and dried with Na₂SO₄. Evaporation and purification by column chromatography afforded 2-(6-phenylpyridin-3-yl)acetonitrile: LCMS $t_R$=1.15 Min (5 min run, $UV_{254nm}$), Mass calculated for, M+194.0, observed LC/MS m/z 195.0 (M+H).

Step 2: Preparation of 4-(6-phenylpyridin-3-yl)-1H-pyrazol-5-amine was used without further purification: LCMS $t_R$=0.91 Min (5 min run, $UV_{254nm}$), Mass calculated for, M+236.1, observed LC/MS m/z 237.1 (M+H).

Step 3: Preparation of 3-(6-phenylpyridin-3-yl)-6,7-dihydro-5H-pyrazolo[1,5-a]pyrrolo[3,4-d]pyrimidin-8-amine

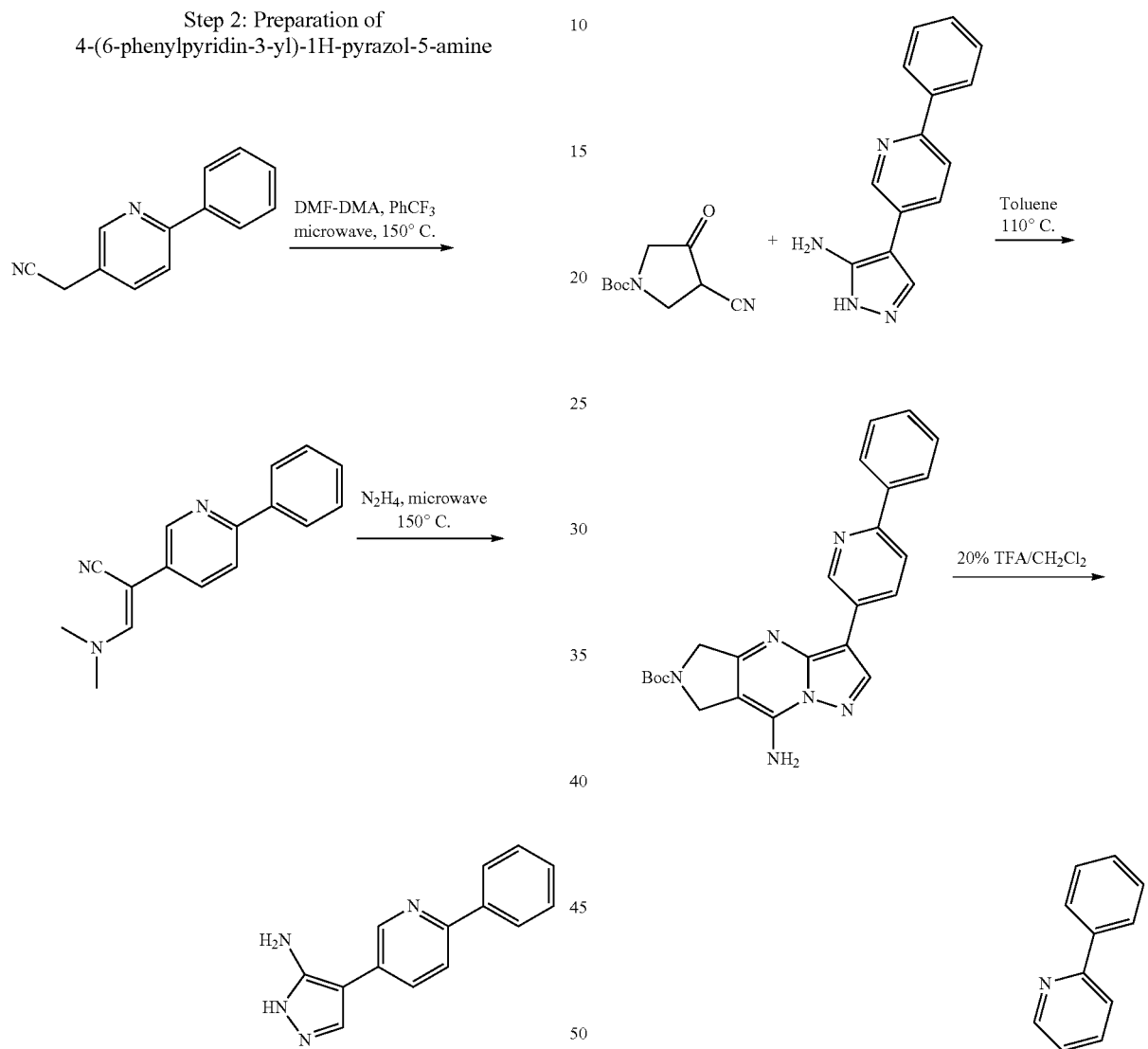

A mixture of 2-(6-phenylpyridin-3-yl)acetonitrile (1940 mg, 10 mmol) in 6 mL of dimethylformamide-dimethlyacetal:DMF:PhCF₃ (1:1:2) was heated under microwave condition at 150° C. for 10 min. LCMS indicated that 2-(6-phenylpyridin-3-yl)acetonitrile was consumed affording 3-(dimethylamino)-2-(6-phenylpyridin-3-yl)acrylonitrile: LCMS $t_R$=1.45 Min (5 min run, $UV_{254nm}$), Mass calculated for, M+249.1, observed LC/MS m/z 250.1 (M+H).

Hydrazine (330 μL, 20.1 mmol) was then added and the reaction was heated under microwave condition at 150° C. for 30 min. The mixture was diluted with H₂O and then extracted with ethyl acetate (×2). The combined organic layers were washed with brine and dried with Na₂SO₄. Evaporation provided 4-(6-phenylpyridin-3-yl)-1H-pyrazol-5-amine which A mixture of tert-butyl 3-cyano-4-oxopyrrolidine-1-carboxylate (60.3 mg, 0.28 mmoL) and 4-(6-phenylpyridin-3-yl)-1H-pyrazol-5-amine (67.8 mg, 0.28 mmoL) in toluene (5 mL) was heated at 115° C. overnight. Concentration afforded crude tert-butyl 8-amino-3-(6-phenylpyridin-3-yl)-5H-pyrazolo[1,5-a]pyrrolo[3,4-d]pyrimidine-6(7H)-carboxylate, which was converted to 3-(6-phenylpyridin-3-yl)-6,7-dihydro-5H-pyrazolo[1,5-a]pyrrolo[3,4-d]pyrimidin-8-amine by the treatment of 20% TFA/CH₂Cl₂ at room temperature:

LCMS $t_R$=0.38 Min (5 min run, $UV_{254nm}$), Mass calculated for, M+328.1, observed LC/MS m/z 329.2 (M+H).

Step 4: Preparation of (R)-1-(8-amino-3-(6-phenylpyridin-3-yl)-5H-pyrazolo[1,5-a]pyrrolo[3,4-d]pyrimidin-6(7H)-yl)-2-hydroxypropan-1-one

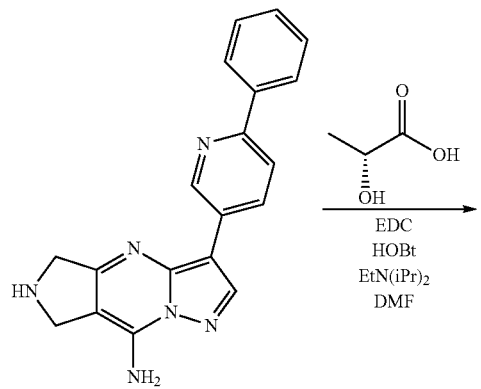

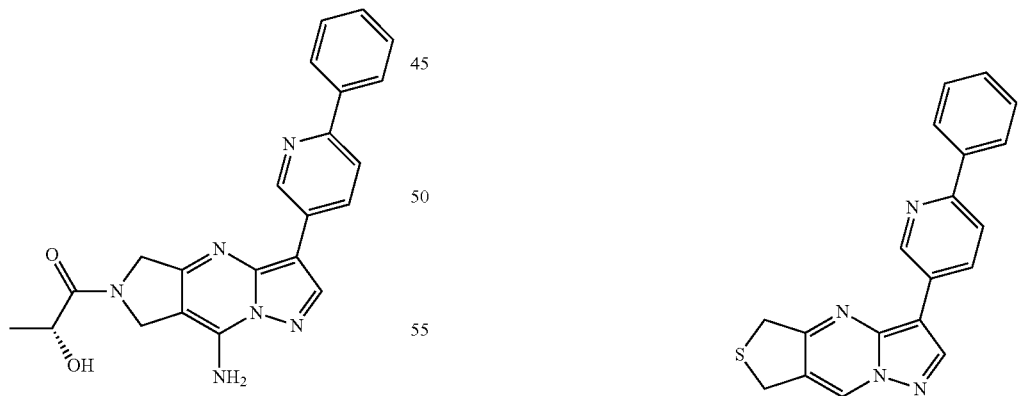

A mixture of crude 3-(6-phenylpyridin-3-yl)-6,7-dihydro-5H-pyrazolo[1,5-a]pyrrolo[3,4-d]pyrimidin-8-amine (0.28 mmol), D-(−)-lactic acid (33.6 mg, 0.37 mmol), EDC (109.7 mg, 0.57 mmol), HOBt (77.6 mg, 0.57 mmol) and DIEA (299.7 uL, 1.72 mmol) in DMF (4 mL) was stirred at room temperature overnight. Purification with prep-LC provided (R)-1-(8-amino-3-(6-phenylpyridin-3-yl)-5H-pyrazolo[1,5-a]pyrrolo[3,4-d]pyrimidin-6(7H)-yl)-2-hydroxypropan-1-one: LCMS $t_R$=2.65 Min (10 min run, $UV_{254nm}$), Mass calculated for, M+400.1, observed LC/MS m/z 401.1 (M+H).

Example 2

Preparation of 3-(6-phenylpyridin-3-yl)-5,7-dihydropyrazolo[1,5-a]6,6-dioxidothieno[3,4-d]pyrimidin-8-amine Step 1: Preparation of 3-(6-phenylpyridin-3-yl)-5,7-dihydropyrazolo[1,5-a]thieno[3,4-d]pyrimidin-8-amine

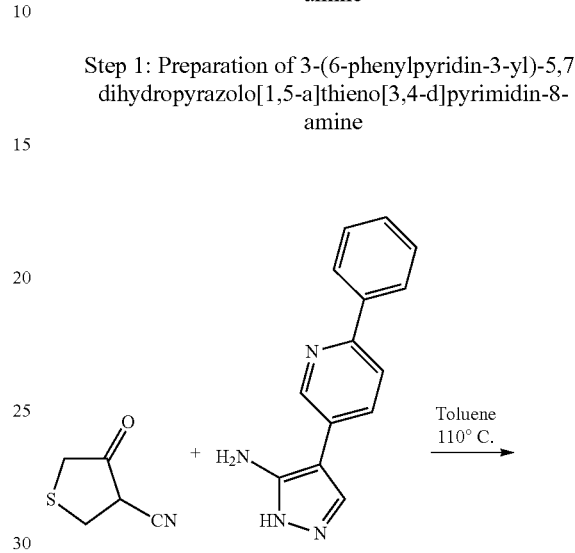

A mixture of 4-oxotetrahydrothiophene-3-carbonitrile (77.6 mg, 0.61 mmol) and 4-(6-phenylpyridin-3-yl)-1H-pyrazol-5-amine (144 mg, 0.61 mmol) in toluene (10 mL) was heated at 115° C. overnight. Concentration and purification with prep-LC provided 3-(6-phenylpyridin-3-yl)-5,7-dihydropyrazolo[1,5-a]thieno[3,4-d]pyrimidin-8-amine:

LCMS $t_R$=1.48 Min (5 min run, $UV_{254nm}$), Mass calculated for, M+345.1, observed LC/MS m/z 346.1 (M+H).

Step 2: Preparation of 3-(6-phenylpyridin-3-yl)-5,7-dihydropyrazolo[1,5-a]6,6-dioxidothieno[3,4-d]pyrimidin-8-amine

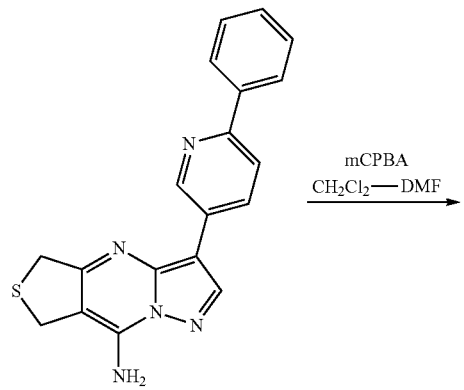

A mixture of 3-(6-phenylpyridin-3-yl)-5,7-dihydropyrazolo[1,5-a]thieno[3,4-d]pyrimidin-8-amine (15 mg, 0.044 mmol) and mCPBA (20.4 mg, 77%, 0.091 mmol) in $CH_2Cl_2$ (3 mL) and DMF (1 mL) was stirred at room temperature for 2 h. Concentration and purification with prep-LC provided 3-(6-phenylpyridin-3-yl)-5,7-dihydropyrazolo[1,5-a]6,6-dioxidothieno[3,4-d]pyrimidin-8-amine: LCMS $t_R$=2.94 Min (10 min run, $UV_{254nm}$), Mass calculated for, M+377.0, observed LC/MS m/z 378.09 (M+H).

Example 3

Preparation of 3-(6-phenylpyridin-3-yl)-N5-(tetrahydro-2H-pyran-4-yl)-6,7-dihydro-5H-cyclopenta[d]pyrazolo[1,5-a]pyrimidine-5,8-diamine

Step 1: Preparation of ethyl 2-(3-cyanopropyl)-1,3-dithiolane-2-carboxylate

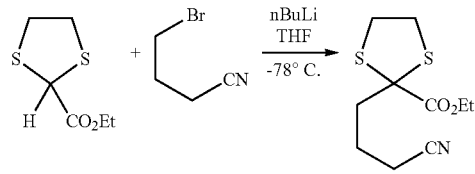 [SMILES: CCOC(=O)C1SCCS1 ; N#CCCCBr ; CCOC(=O)C1(CCCC#N)SCCS1]

n-Butyllithium (6.5 mL, 1.6 M in hexane) was added to a solution of ethyl 1,3-dithiolane-2-carboxylate (1925 mg, 10 mmol) in THF (10 mL) at −78° C. under $N_2$. The reaction mixture was stirred for 30 min at −78° C. and then 4-bromobutanenitrile (1469 mg, 10 mmol) in THF (10 mL) was added. The mixture was warmed to room temperature and stirred for 30 min. It was diluted with diethyl ether and washed with 1 N HCl and $H_2O$, and dried. Evaporation and purification by column chromatography afforded ethyl 2-(3-cyanopropyl)-1,3-dithiolane-2-carboxylate: LCMS $t_R$=1.86 Min (5 min run, $UV_{254nm}$), Mass calculated for, M+259.0, observed LC/MS m/z 260.0 (M+H).

Step 2: Preparation of 6-oxo-1,4-dithiaspiro[4.4]nonane-7-carbonitrile

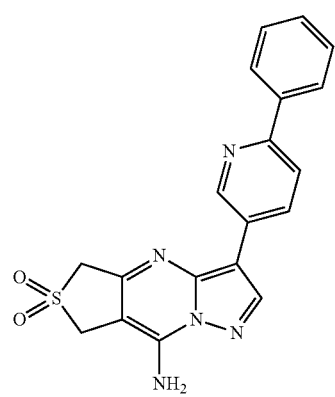

A mixture of NaH (60%, 31.8 mg, 0.79 mmol) and ethyl 2-(3-cyanopropyl)-1,3-dithiolane-2-carboxylate (171.5 mg, 0.66 mmol) in dioxane (5 mL) was heated at 100° C. overnight. The mixture was diluted with $H_2O$ and then extracted with ethyl acetate (×2). The combined organic layers were washed with brine, dried with $Na_2SO_4$, and evaporated to afford crude 6-oxo-1,4-dithiaspiro[4.4]nonane-7-carbonitrile: LCMS $t_R$=1.67 Min (5 min run, $UV_{254nm}$), Mass calculated for, M+213.0, observed LC/MS m/z 214.1 (M+H).

Step 3: Preparation of 8-amino-3-(6-phenylpyridin-3-yl)-6,7-dihydro-5H-cyclopenta[d]pyrazolo[1,5-a]pyrimidin-5-one

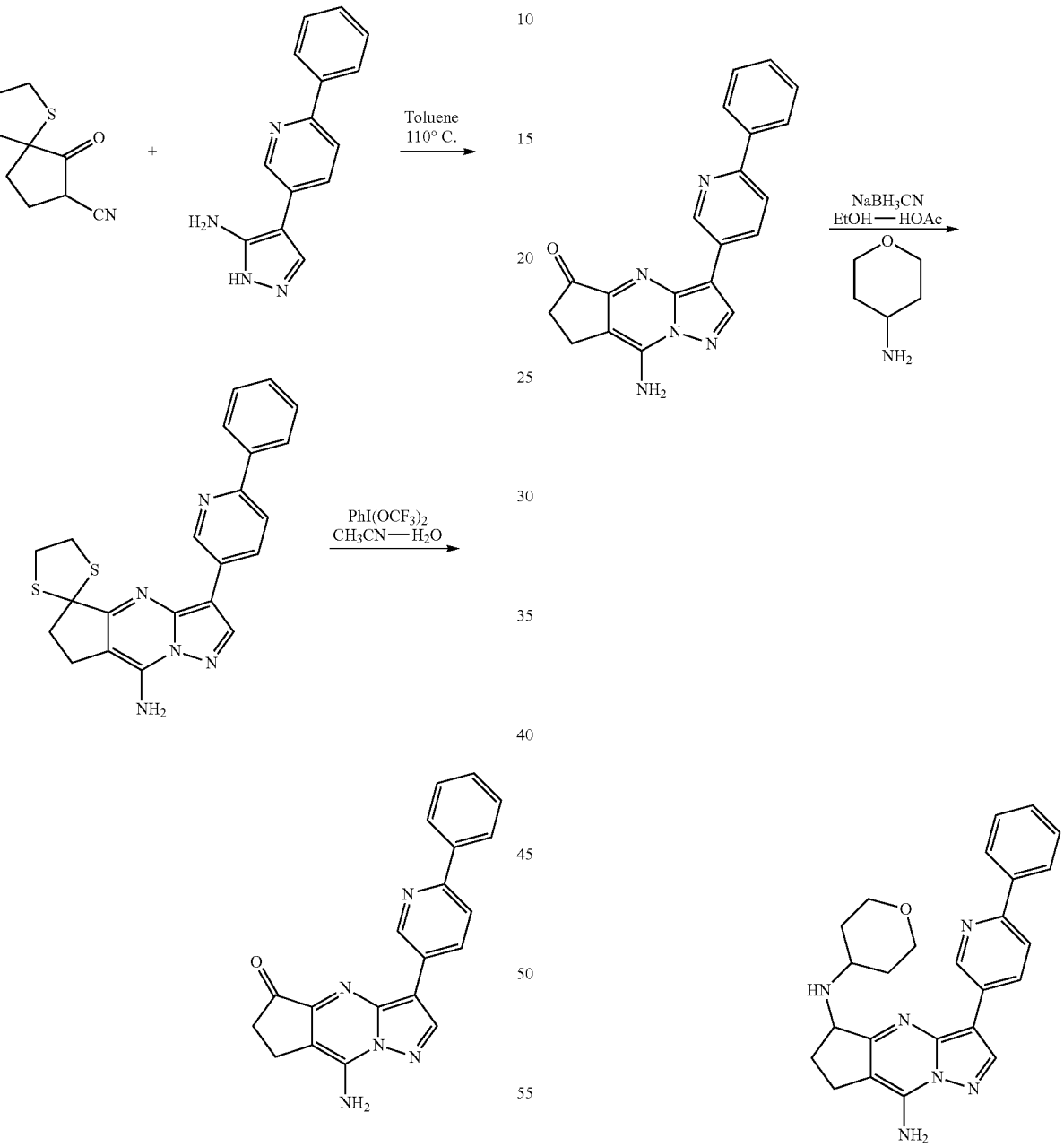

A mixture of 6-oxo-1,4-dithiaspiro[4.4]nonane-7-carbonitrile (485 mg, 2.27 mmol) and 4-(6-phenylpyridin-3-yl)-1H-pyrazol-5-amine (537 mg, 2.27 mmol) in toluene (10 mL) was heated at 115° C. overnight. Concentration afforded crude 3-(6-phenylpyridin-3-yl)-6,7-dihydrospiro[cyclopenta[d]pyrazolo[1,5-a]pyrimidine-5,2'-[1,3]dithiolan]-8-amine, which was converted to 8-amino-3-(6-phenylpyridin-3-yl)-6,7-dihydro-5H-cyclopenta[d]pyrazolo[1,5-a]pyrimidin-5-one applying Stork's procedure (G. Stork, K. Zhao, *Tetrahedron Letter*, 1989, 30, 287) by treating with PhI(OCF$_3$)$_2$.

LCMS $t_R$=1.07 Min (5 min run, $UV_{254nm}$), Mass calculated for, M+341.1, observed LC/MS m/z 342.1 (M+H).

Step 4: Preparation of 3-(6-phenylpyridin-3-yl)-N5-(tetrahydro-2H-pyran-4-yl)-6,7-dihydro-5H-cyclopenta[d]pyrazolo[1,5-a]pyrimidine-5,8-diamine A mixture of 8-amino-3-(6-phenylpyridin-3-yl)-6,7-dihydro-5H-cyclopenta[d]pyrazolo[1,5-a]pyrimidin-5-one (61.5 mg, 0.18 mmol), tetrahydro-2H-pyran-4-amine (100 uL), HOAc (100 uL) in EtOH (2 mL) was stirred at room temperature for 15 min. NaBH$_3$CN (56.7 mg, 0.90 mmol) was added and the reaction was stirred overnight. Purification with prep-LC provided 3-(6-phenylpyridin-3-yl)-N5-(tetrahydro-2H-pyran-4-yl)-6,7-dihydro-5H-cyclopenta[d]pyrazolo[1,5-a]

pyrimidine-5,8-diamine: LCMS $t_R$=2.35 Min (10 min run, $UV_{254nm}$), Mass calculated for, M+426.0, observed LC/MS m/z 427.0 (M+H).

Example 4

Preparation of 1-(4-(8-amino-3-(6-fluoroquinolin-3-yl)-7-methyl-5H-pyrazolo[1,5-a]pyrrolo[2,3-d]pyrimidin-5-yl)piperidin-1-yl)-2-hydroxyethanone Step 1: Preparation of pyrazolo[1,5-a]pyrimidine-5,7-diol

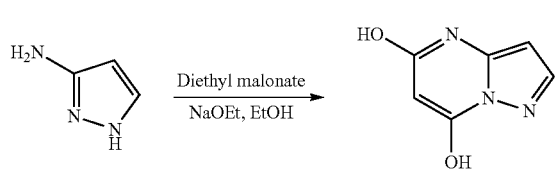 [SMILES: Nc1cc[nH]n1 ; Oc1cc(O)n2nccc2n1]

To 1H-pyrazol-3-amine (12.3 g, 148.0 mmol) in EtOH (50 mL) was added diethyl malonate (25.0 mL, 164.7 mmol), 21 wt % NaOEt in EtOH (110 mL, 294.6 mmol) and additional EtOH (50 mL). The resulting mixture was then heated at 80° C. under an atmosphere of argon for 16 hours, at which time the reaction was allowed to cool to room temperature. The reaction mixture was then concentrated in vacuo until almost dry, before $H_2O$ (500 mL) was added. Vigorous stirring aided the dissolving of solids, at which time conc. HCl was added until pH~2 was attained (solid precipitate formed). The precipitate was collected and dried by vacuum filtration giving pyrazolo[1,5-a]pyrimidine-5,7-diol as a tan solid.

Step 2: Preparation of 5,7-dichloropyrazolo[1,5-a]pyrimidine

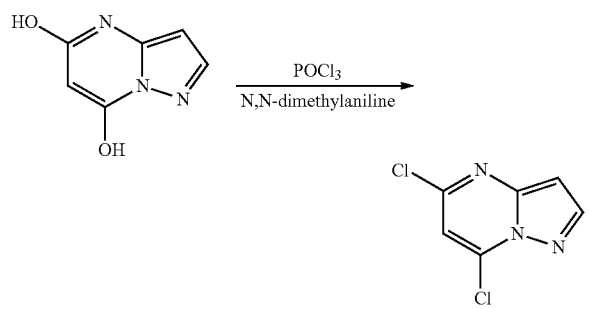

To pyrazolo[1,5-a]pyrimidine-5,7-diol (9.6 g, 63.5 mmol) in a 500 mL flask was added POCl₃ (125 mL, 1341.1 mmol). The flask was then cooled to 0° C. and N,N-dimethylaniline (22 mL, 173.6 mmol) was carefully added. On warming to room temperature, the reaction was then heated at 60° C. under an atmosphere of argon for 16 hours. On cooling, the reaction mixture was concentrated in vacuo to give a brown viscous liquid. This brown viscous liquid was carefully poured onto ice and allowed to warm to room temperature overnight. To the brown solution was carefully added saturated $NaHCO_3$ solution until no further effervescence was observed and pH~8 was attained. Organics were then extracted with $CH_2Cl_2$ (4×50 mL), dried ($Na_2SO_4$) and concentrated in vacuo to give a brown liquid. Gradient column chromatography on silica eluting with 50% $CH_2Cl_2$/hexanes (to elute aniline) followed by 75% $CH_2Cl_2$/hexanes (to elute product) gave 5,7-dichloropyrazolo[1,5-]pyrimidine as a white solid.

Step 3: Preparation of 5-chloropyrazolo[1,5-a]pyrimidin-7-amine

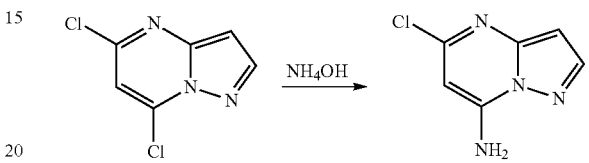

To 5,7-dichloropyrazolo[1,5-a]pyrimidine (7.6 g, 40.4 mmol) in a sealed vessel was added $NH_4OH$ (100 mL). The vessel was then sealed and heated at 85° C. for 2.5 hours, at which time the consistency of the white solid had changed (from foamy white solid to free-flowing white solid). The vessel was removed from the heat source and allowed to cool to room temperature overnight. On cooling, the contents of the vessel were collected and dried by vacuum filtration giving 5-chloropyrazolo[1,5-a]pyrimidin-7-amine as a yellow-tinged white solid.

Step 4: Preparation of 5-chloro-N,N-bis((2-(trimethylsilyl)ethoxy)methyl)pyrazolo[1,5-a]pyrimidin-7-amine

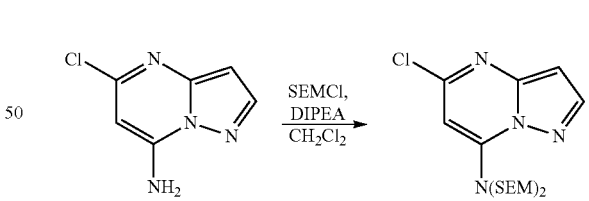

To 5-chloropyrazolo[1,5-a]pyrimidin-7-amine (6.7 g, 39.7 mmol) in $CH_2Cl_2$ (30 mL) was added N,N-diisopropylethylamine (48.0 mL, 275.6 mmol) followed by 2-(Trimethylsilyl)ethoxymethyl chloride (25.0 mL, 141.7 mmol). The reaction was heated at 45° C. for 3 hours before being allowed to cool to room temperature. The reaction mixture was then poured into a separatory funnel containing ~100 mL saturated $NaHCO_3$ solution and $CH_2Cl_2$ (50 mL). Organics were then extracted with $CH_2Cl_2$ (4×50 mL), dried ($Na_2SO_4$) and concentrated in vacuo to give a thick orange liquid. Gradient column chromatography on silica eluting with 5% to 15%

EtOAc/hexanes gave crude 5-chloro-N,N-bis((2-(trimethylsilyl)ethoxy)methyl)pyrazolo[1,5-a]pyrimidin-7-amine as a colorless liquid.

Step 5: Preparation of 5-chloro-3-iodo-N,N-bis((2-(trimethylsilyl)ethoxy)methyl)pyrazolo[1,5-a]pyrimidin-7-amine

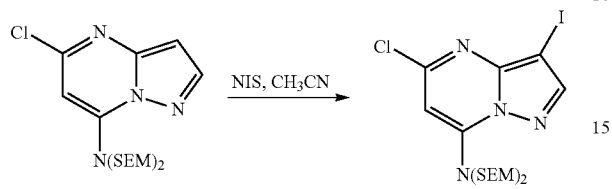

To 5-chloro-N,N-bis((2-(trimethylsilyl)ethoxy)methyl)pyrazolo[1,5-a]pyrimidin-7-amine (7.9 g) in CH₃CN (100 mL) was added N-iodosuccinimide (4.3 g, 19.2 mmol) and the resulting mixture was stirred at room temperature for 30 min, at which time LC/MS confirmed full conversion of starting material to product. Saturated sodium thiosulfate solution (~20 mL) was added and stirring continued for 5 minutes before the reaction mixture was transferred to a separatory funnel using CH₂Cl₂ (30 mL) and H₂O (30 mL). Brine (50 mL) was added and organics were extracted with CH₂Cl₂ (4×40 mL), dried (Na₂SO₄) and concentrated in vacuo to give crude 5-chloro-3-iodo-N,N-bis((2-(trimethylsilyl)ethoxy)methyl)pyrazolo[1,5-a]pyrimidin-7-amine as a light brown liquid.

Step 6: Preparation of 5-chloro-3-(6-fluoroquinolin-3-yl)-N,N-bis((2-(trimethylsilyl)ethoxy)methyl)pyrazolo[1,5-a]pyrimidin-7-amine

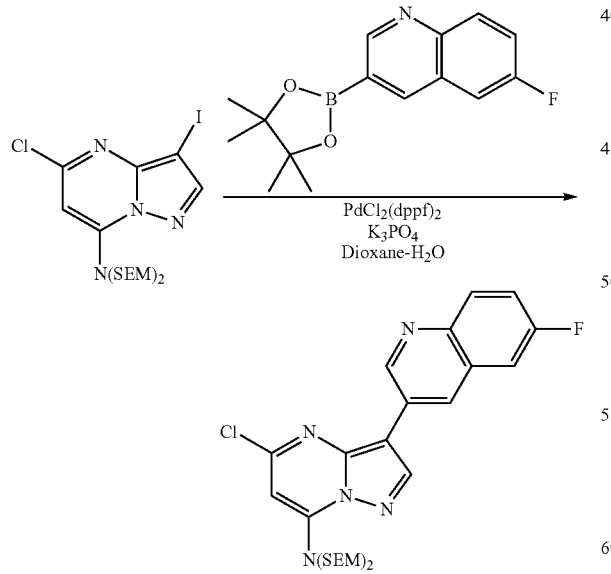

6-fluoro-3-(4,4,5,5-tetramethyl-1,3,2-dioxaborolan-2-yl)quinoline (996.4 mg, 3.65 mmol), K₃PO₄ (1933.6 mg, 9.12 mmol), and PdCl₂(dppf).CH₂Cl₂ (248 mg, 0.30 mmol) was added to a solution of 5-chloro-3-iodo-N,N-bis((2-(trimethylsilyl)ethoxy)methyl)pyrazolo[1,5-a]pyrimidin-7-amine (1684.3 mg, 3.04 mmol) in dioxane (18 mL) and H₂O (3 mL). The resulting mixture was stirred at 80° C. under argon overnight. The mixture was diluted with H₂O and then extracted with ethyl acetate (×2). The combined organic layers were washed with brine and dried with Na₂SO₄. Evaporation and purification by column chromatography afforded 5-chloro-3-(6-fluoroquinolin-3-yl)-N,N-bis((2-(trimethylsilyl)ethoxy)methyl)pyrazolo[1,5-a]pyrimidin-7-amine: LCMS $t_R$=3.34 Min (5 min run, UV$_{254nm}$), Mass calculated for, M+573.2, observed LC/MS m/z 574.2 (M+H).

Step 7: Preparation of tert-butyl 4-(7-(bis((2-(trimethylsilyl)ethoxy)methyl)amino)-3-(6-fluoroquinolin-3-yl)pyrazolo[1,5-a]pyrimidin-5-ylamino)piperidine-1-carboxylate

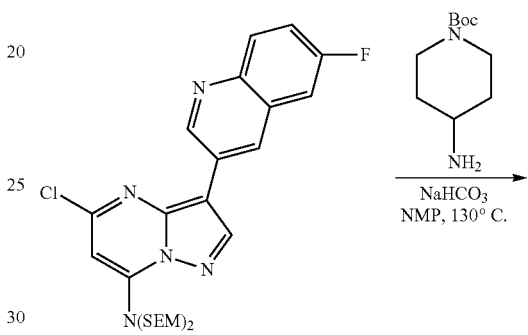

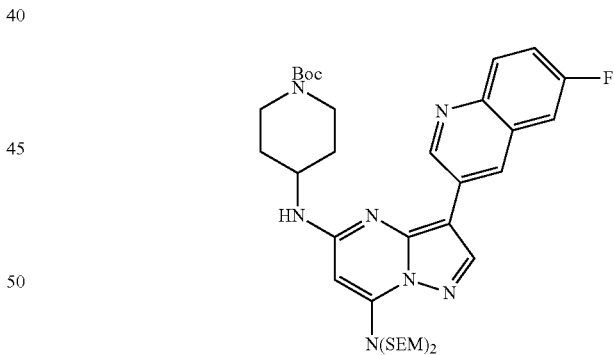

A mixture of 5-chloro-3-(6-fluoroquinolin-3-yl)-N,N-bis((2-(trimethylsilyl)ethoxy)methyl)pyrazolo[1,5-a]pyrimidin-7-amine (531.3 mg, 0.93 mmol), tert-butyl 4-aminopiperidine-1-carboxylate (556.6 mg, 2.78 mmol), NaHCO₃ (467.2 mg, 5.56 mmol) in NMP (10 mL) was heated at 130° C. overnight. The mixture was cooled to room temperature and diluted with H₂O and then extracted with ethyl acetate (×2). The combined organic layers were washed with brine and dried with Na₂SO₄. Evaporation of solvent afforded the crude displacement compound. Purification by column chromatography afforded tert-butyl 4-(7-(bis((2-(trimethylsilyl)ethoxy)methyl)amino)-3-(6-fluoroquinolin-3-yl)pyrazolo[1,5-a]pyrimidin-5-ylamino)piperidine-1-carboxylate: LCMS $t_R$=3.24 Min (5 min run, $UV_{254nm}$), Mass calculated for M+737.4, observed m/z 738.3 (M+H).

Step 8: Preparation of tert-butyl 4-(7-(bis((2-(trimethylsilyl)ethoxy)methyl)amino)-6-bromo-3-(6-fluoroquinolin-3-yl)pyrazolo[1,5-a]pyrimidin-5-ylamino)piperidine-1-carboxylate

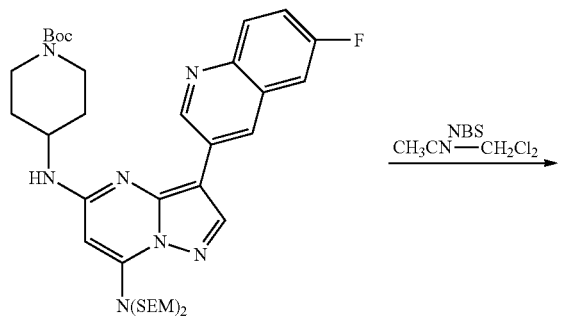

5-ylamino)piperidine-1-carboxylate: LCMS $t_R$=1.88 Min (5 min run, $UV_{254nm}$), Mass calculated for M+815.3, observed m/z 816.1 (M+H).

Step 9: Preparation of tert-butyl 4-(allyl(7-(bis((2-(trimethylsilyl)ethoxy)methyl)amino)-6-bromo-3-(6-fluoroquinolin-3-yl)pyrazolo[1,5-a]pyrimidin-5-yl)amino)piperidine-1-carboxylate

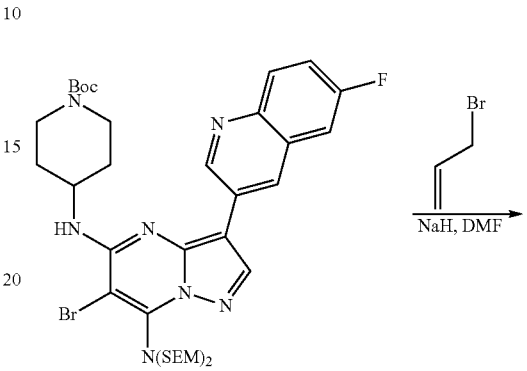

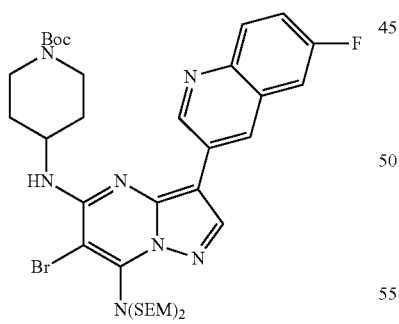

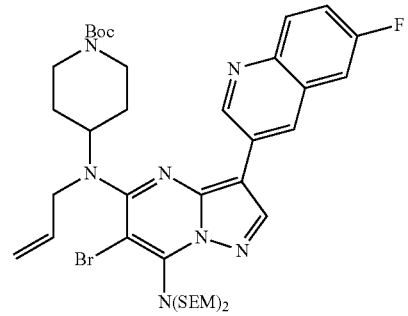

NBS (410.9 mg, 2.31 mmol) was added to a solution of tert-butyl 4-(7-(bis((2-(trimethylsilyl)ethoxy)methyl)amino)-3-(6-fluoroquinolin-3-yl)pyrazolo[1,5-a]pyrimidin-5-ylamino)piperidine-1-carboxylate (1547 mg, 2.09 mmol) in $CH_3CN$ (50 mL) and $CH_2Cl_2$ (50 mL). After stirring at room temperature for 2 h, the mixture was concentrated in vacuo. Purification by column chromatography afforded tert-butyl 4-(7-(bis((2-(trimethylsilyl)ethoxy)methyl)amino)-6-bromo-3-(6-fluoroquinolin-3-yl)pyrazolo[1,5-a]pyrimidin- At 0° C., NaH (60%, 40.2 mg, 1.00 mmol) was added in one portion to a solution of tert-butyl 4-(7-(bis((2-(trimethylsilyl)ethoxy)methyl)amino)-6-bromo-3-(6-fluoroquinolin-3-yl)pyrazolo[1,5-a]pyrimidin-5-ylamino)piperidine-1-carboxylate (205 mg, 0.25 mmol) in DMF (6 mL). After stirring at room temperature for 30 min, the mixture was cooled to 0° C. and allyl bromide (60.8 mg, 0.50 mmol) was added dropwise. The mixture was stirred at room temperature overnight and then diluted with $H_2O$ and then extracted with ethyl acetate (×2). The combined organic layers were washed with brine and dried with $Na_2SO_4$. Evaporation and purification by column chromatography afforded tert-butyl 4-(allyl(7-(bis((2-(trimethylsilyl)ethoxy)methyl)amino)-6-bromo-3-(6-fluoroquinolin-3-yl)pyrazolo[1,5-a]pyrimidin-5-yl)

amino)piperidine-1-carboxylate: LCMS $t_R$=1.99 Min (5 min run, $UV_{254nm}$), Mass calculated for M+855.3, observed LC/MS m/z 856.3 (M+H).

Step 10: Preparation of tert-butyl 4-(8-(bis((2-(trimethylsilyl)ethoxy)methyl)amino)-3-(6-fluoroquinolin-3-yl)-7-methyl-5H-pyrazolo[1,5-a]pyrrolo[2,3-d]pyrimidin-5-yl)piperidine-1-carboxylate

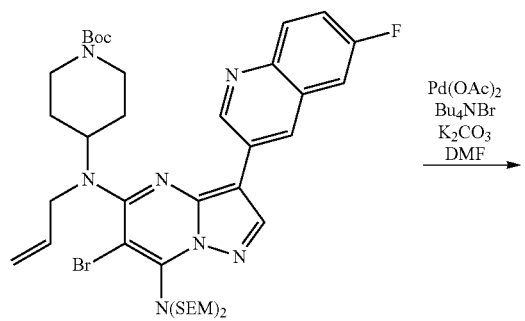

A degassed mixture of tert-butyl 4-(allyl(7-(bis((2-(trimethylsilyl)ethoxy)methyl)amino)-6-bromo-3-(6-fluoroquinolin-3-yl)pyrazolo[1,5-a]pyrimidin-5-yl)amino)piperidine-1-carboxylate (163 mg, 0.19 mmol), Pd(OAc)₂ (4.3 mg, 0.02 mmol), Bu₄NBr (73.6 mg, 0.23 mmol), and K₂CO₃ (78.7 mg, 0.57 mmol) in DMF (6 mL) was heated at 90° C. for 3 h. After cooling to room temperature, the mixture was diluted with H₂O and then extracted with ethyl acetate (×2). The combined organic layers were washed with brine and dried with Na₂SO₄. Evaporation and purification by column chromatography afforded tert-butyl 4-(8-(bis((2-(trimethylsilyl)ethoxy)methyl)amino)-3-(6-fluoroquinolin-3-yl)-7-methyl-5H-pyrazolo[1,5-a]pyrrolo[2,3-d]pyrimidin-5-yl)

piperidine-1-carboxylate: LCMS $t_R$=1.96 Min (5 min run, $UV_{254nm}$), Mass calculated for M+775.4, observed LC/MS m/z 776.0 (M+H).

Step 11: Preparation of 3-(6-fluoroquinolin-3-yl)-7-methyl-5-(piperidin-4-yl)-5H-pyrazolo[1,5-a]pyrrolo[2,3-d]pyrimidin-8-amine

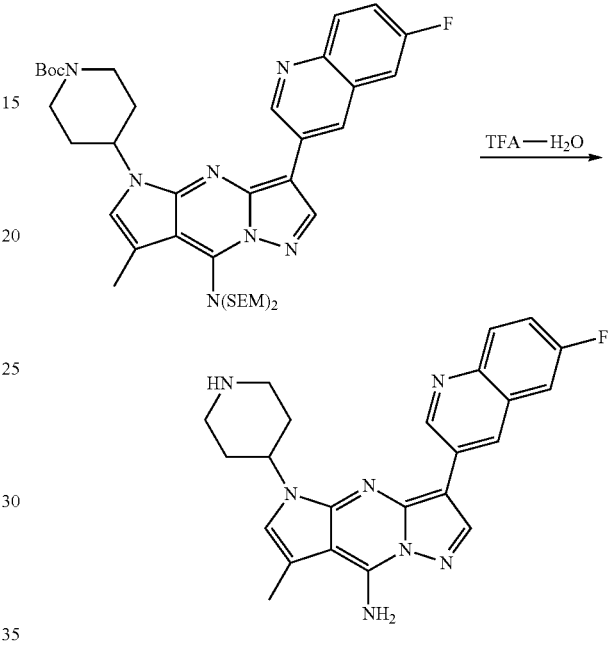

At 0° C., tert-butyl 4-(8-(bis((2-(trimethylsilyl)ethoxy)methyl)amino)-3-(6-fluoroquinolin-3-yl)-7-methyl-5H-pyrazolo[1,5-a]pyrrolo[2,3-d]pyrimidin-5-yl)piperidine-1-carboxylate (95 mg, 0.12 mmol) was treated with 80% TFA/H₂O (5 mL). After stirring at room temperature for 30 min, concentration afforded crude 3-(6-fluoroquinolin-3-yl)-7-methyl-5-(piperidin-4-yl)-5H-pyrazolo[1,5-a]pyrrolo[2,3-d]pyrimidin-8-amine which was used for next step without further purification. LCMS is =0.69 Min (5 min run, $UV_{254nm}$), Mass calculated for M+415.2, observed m/z 416.2 (M+H).

Step 12: Preparation of 9-amino-3-(6-fluoroquinolin-3-yl)-5-(1-(2-hydroxyacetyl)piperidin-4-yl)pyrazolo[1,5-a]pyrido[2,3-d]pyrimidin-6(5H)-one

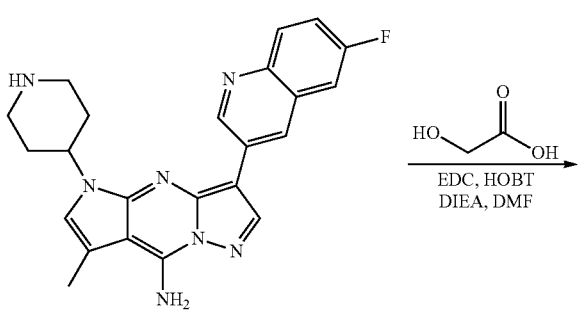

49

-continued

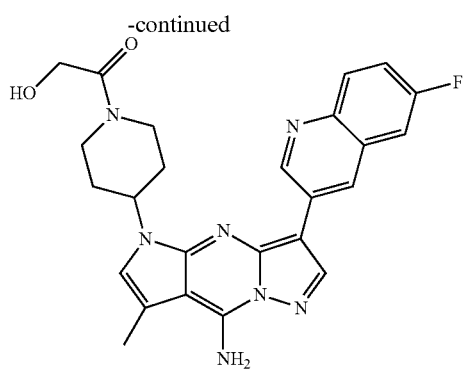

A mixture of crude 3-(6-phenylpyridin-3-yl)-6,7-dihydro-5H-pyrazolo[1,5-a]pyrrolo[3,4-d]pyrimidin-8-amine (34.0 mg, 0.08 mmol), 2-hydroxyacetic acid (7.5 mg, 0.10 mmoL), EDC (31.3 mg, 0.16 mmol), HOBt (22.1 mg, 0.16 mmol) and DMA (85.5 uL, 0.49 mmol) in DMF (4 mL) was stirred at room temperature for 2 h. Purification with prep-LC provided 1-(4-(8-amino-3-(6-fluoroquinolin-3-yl)-7-methyl-5H-pyrazolo[1,5-a]pyrrolo[2,3-d]pyrimidin-5-yl)piperidin-1-yl)-2-hydroxyethanone: LCMS $t_R$=2.63 Min (10 min run, $UV_{254nm}$), Mass calculated for, M+473.2, observed LC/MS m/z 474.1 (M+H).

Examples 5-15

By applying the chemistry described in Example 4, and using suitable starting material, the following compounds were synthesized.

| Example No. | Structures | FW | M + H | Retention Time, 10 min method |
|---|---|---|---|---|
| 5 | 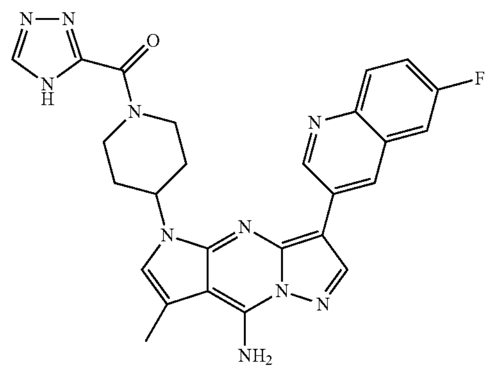 [SMILES: Cc1cn(C2CCN(C(=O)c3nnc[nH]3)CC2)c2nc3c(-c4cnc5ccc(F)cc5c4)cnn3c(N)c12] | 510.2 | 511.1 | 2.49 |
| 6 | 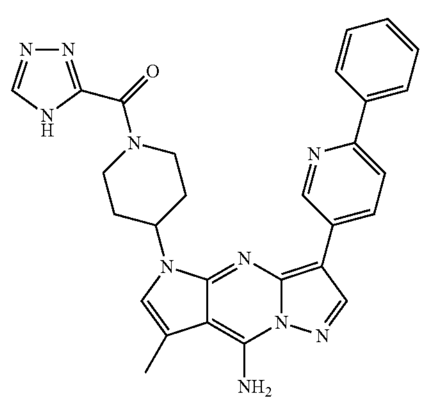 [SMILES: Cc1cn(C2CCN(C(=O)c3nnc[nH]3)CC2)c2nc3c(-c4ccc(-c5ccccc5)nc4)cnn3c(N)c12] | 518.2 | 519.0 | 2.22 |

-continued

| Example No. | Structures | FW | M + H | Retention Time, 10 min method |
|---|---|---|---|---|
| 7 | 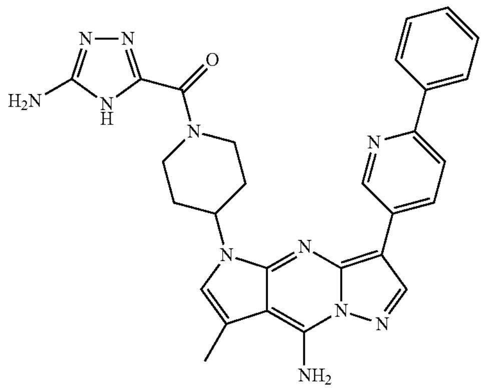 [SMILES: Cc1cn(C2CCN(C(=O)c3nnc(N)[nH]3)CC2)c2nc3c(-c4ccc(-c5ccccc5)nc4)cnn3c(N)c12] | 533.2 | 534.2 | 2.16 |
| 8 | 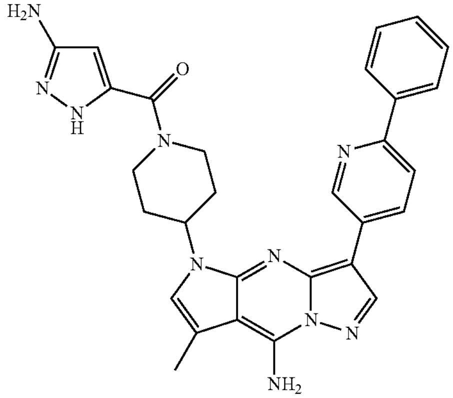 [SMILES: Cc1cn(C2CCN(C(=O)c3cc(N)n[nH]3)CC2)c2nc3c(-c4ccc(-c5ccccc5)nc4)cnn3c(N)c12] | 532.2 | 533.2 | 2.27 |
| 9 | 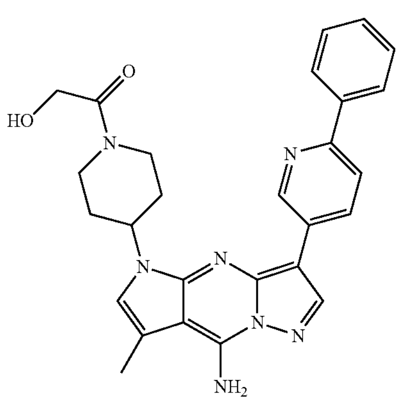 [SMILES: Cc1cn(C2CCN(C(=O)CO)CC2)c2nc3c(-c4ccc(-c5ccccc5)nc4)cnn3c(N)c12] | 481.2 | 482.2 | 2.39 |

-continued
| Example No. | Structures | FW | M + H | Retention Time, 10 min method |
|---|---|---|---|---|
| 10 | 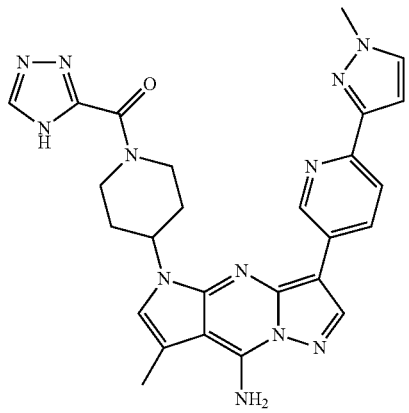 [SMILES: Cc1cn(C2CCN(C(=O)c3nnc[nH]3)CC2)c2nc3c(-c4ccc(-c5ccn(C)n5)nc4)cnn3c(N)c12] | 522.2 | 523.2 | 1.95 |
| 11 | 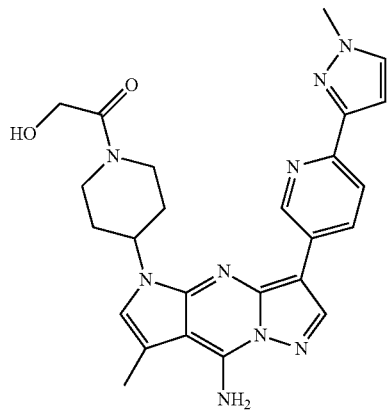 [SMILES: Cc1cn(C2CCN(C(=O)CO)CC2)c2nc3c(-c4ccc(-c5ccn(C)n5)nc4)cnn3c(N)c12] | 485.2 | 486.2 | 1.97 |
| 12 | 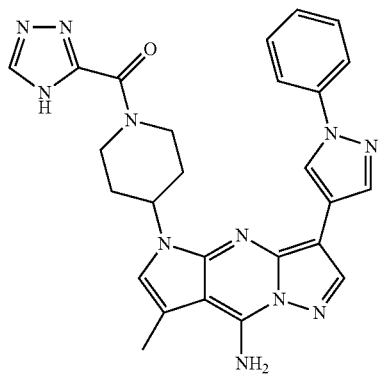 | 507.2 | 508.0 | 2.79 |

| Example No. | Structures | FW | M + H | Retention Time, 10 min method |
|---|---|---|---|---|
| 13 | 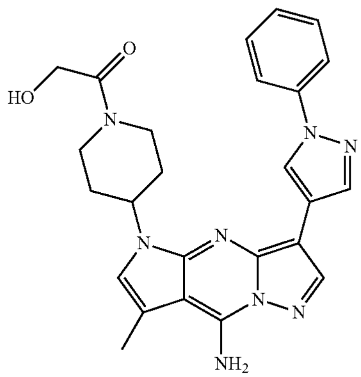 [SMILES: Cc1cn(C2CCN(C(=O)CO)CC2)c2nc3c(-c4cnn(-c5ccccc5)c4)cnn3c(N)c12] | 470.2 | 471.0 | 2.88 |
| 14 | 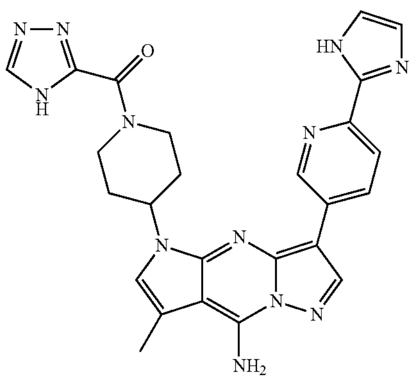 [SMILES: Cc1cn(C2CCN(C(=O)c3nnc[nH]3)CC2)c2nc3c(-c4ccc(-c5ncc[nH]5)nc4)cnn3c(N)c12] | 508.2 | 509.2 | 1.74 |
| 15 | 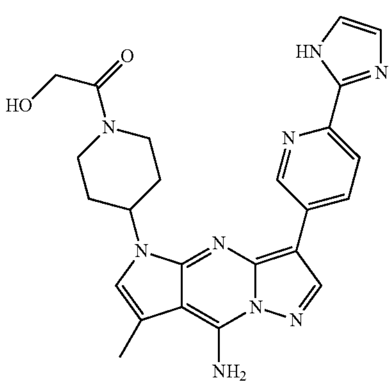 [SMILES: Cc1cn(C2CCN(C(=O)CO)CC2)c2nc3c(-c4ccc(-c5ncc[nH]5)nc4)cnn3c(N)c12] | 471.2 | 472.1 | 1.77 |

Pharmaceutical Composition

As a specific embodiment of this invention, 100 mg of (R)-1-(8-amino-3-(6-phenylpyridin-3-yl)-5H-pyrazolo[1,5-a]pyrrolo[3,4-d]pyrimidin-6(7H)-yl)-2-hydroxypropan-1-one, is formulated with sufficient finely divided lactose to provide a total amount of 580 to 590 mg to fill a size 0, hard-gelatin capsule.

Assays

The compounds of the instant invention described in the Examples were tested by the assays described below and were found to have mTOR inhibitory activity. Other assays are known in the literature and could be readily performed by those of skill in the art.

mTOR Kinase Assay

The mTOR assay buffer contains 10 mM hepes (pH 7.4), 50 mM NaCl, 100 μg/ml BSA, 50 mM B-glycerophosphate, 10 mM MnCl2 and 0.5 mM DTT. 20 ng of mTOR enzyme is preincubated with the compound for 10 minutes. 5 μM ATP and 0.1 μM GSTS6K is added. The reaction is incubated for one hour at 30° C. Anti phospho p70S6K (about 1.7 ng/well) and anti GSTXL665 (1:1 Ratio with the substrate GSTS6K) are added after incubating. The plates are read at least 2 hours after adding the anti phospho p70S6K and the anti GSTXL665.

$IC_{50}$ determinations:

Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate IC$_{50}$ values, the dose-response curves were then fitted to a standard sigmoidal curve and IC$_{50}$ values were derived by nonlinear regression analysis.

CHK1 In Vitro Kinase Assay

This in vitro assay utilizes recombinant His-CHK1 expressed in the baculovirus expression system as an enzyme source and a biotinylated peptide based on CDC25C as substrate (biotin-RSGLYRSPSMPENLNRPR (SEQ ID NO: 1)).

Materials and Reagents:

1) CDC25C Ser 216 C-term Biotinylated peptide substrate (25 mg), stored at −20° C., Custom Synthesis by Research Genetics: biotin-RSGLYRSPSMPENLNRPR (SEQ ID NO:1) 2595.4 MW
2) His-CHK1 In House lot P976, 235 μg/mL, stored at −80° C.
3) D-PBS (without CaCl and MgCl): GIBCO, Cat. #14190-144
4) SPA beads: Amersham, Cat. #SPQ0032: 500 mg/vial
5) 96-Well White Microplate with Bonded GF/B filter: Packard, Cat. #6005177
6) Top seal-A 96 well Adhesive Film: Perkin Elmer, Cat. #6005185
7) 96-well Non-Binding White Polystyrene Plate: Corning, Cat. #6005177
8) MgCl$_2$: Sigma, Cat. #M-8266
9) DTT: Promega, Cat. #V3155
10) ATP, stored at 4° C.: Sigma, Cat. #A-5394
11) γ$^{33}$P-ATP, 1000-3000 Ci/mMol: Amersham, Cat. #AH9968
12) NaCl: Fisher Scientific, Cat. #BP358-212
13) H$_3$PO$_4$ 85% Fisher, Cat. #A242-500
14) Tris-HCL pH 8.0: Bio-Whittaker, Cat. #16-015V
15) Staurosporine, 100 μg: CALBIOCHEM, Cat. #569397
16) Hypure Cell Culture Grade Water, 500 mL: HyClone, Cat.# SH30529.02

Reaction Mixtures:

1) Kinase Buffer: 50 mM Tris pH 8.0; 10 mM MgCl$_2$; 1 mM DTT
2) His-CHK1, In House Lot P976, MW ~30 KDa, stored at −80° C.

6 nM is required to yield positive controls of ~5,000 CPM. For 1 plate (100 reaction): dilute 8 μL of 235 μg/mL (7.83 μM) stock in 2 mL Kinase Buffer. This makes a 31 nM mixture. Add 20 μL/well. This makes a final reaction concentration of 6 nM.

3) CDC25C Biotinylated Peptide.

Dilute CDC25C to 1 mg/mL (385 μM) stock and store at −20° C. For 1 plate (100 reactions): dilute 10 μL of 1 mg/mL peptide stock in 2 mL Kinase Buffer. This gives a 1.925 μM mix. Add 20 μL/reaction. This makes a final reaction concentration of 385 nM.

4) ATP Mix.

For 1 plate (100 reactions): dilute 10 μL of 1 mM ATP (cold) stock and 2 μL fresh P33-ATP (20 μCi) in 5 mL Kinase Buffer. This gives a 2 μM ATP (cold) solution; add 50 μL/well to start the reaction. Final volume is 100 μL/reaction so the final reaction concentrations will be 1 μM ATP (cold) and 0.2 μCi/reaction.

5) Stop Solution:

For 1 plate add: To 10 mL Wash Buffer 2 (2M NaCl 1% H$_3$PO$_4$): 1 mL SPA bead slimy (50 mg); Add 100 μL/well
6) Wash buffer 1: 2 M NaCl
7) Wash buffer 2: 2 M NaCl, 1% H$_3$PO$_4$ Assay Procedure:

| Assay Component | Final Concentration | Volume |
| --- | --- | --- |
| CHK1 | 6 nM | 20 μl/rxn |
| Compound (10% DMSO) | — | 10 μl/rxn |
| CDC25C | 0.385 μM | 20 μl/rxn |
| γ$^{33}$P-ATP | 0.2 μCi/rxn | 50 μl/rxn |
| Cold ATP | 1 μM | |
| Stop solution | | 100 μl/rxn* |
| SPA beads | 0.5 mg/rxn | |
| | | 200 μl/rxn** |

*Total reaction volume for assay.
**Final reaction volume at termination of reaction (after addition of stop solution).

1) Dilute test compounds to desired concentrations in water/10% DMSO—this will give a final DMSO concentration of 1% in the reaction. Dispense 10 μL/reaction to appropriate wells. Add 10 μL 10% DMSO to positive (CHK1+CDC25C+ATP) and negative (CHK1+ATP only) control wells.
2) Thaw enzyme on ice—dilute enzyme to proper concentration in kinase buffer (see Reaction Mixtures) and dispense 20 μL to each well.
3) Thaw the Biotinylated substrate on ice and dilute in kinase buffer (see Reaction Mixtures). Add 20 μL/well except to negative control wells. Instead, add 20 μL Kinase Buffer to these wells.
4) Dilute ATP (cold) and P33-ATP in kinase buffer (see Reaction Mixtures). Add 50 μL/well to start the reaction.
5) Allow the reaction to run for 2 hours at room temperature.
6) Stop reaction by adding 100 μL of the SPA beads/stop solution (see Reaction Mixtures) and leave to incubate for 15 minutes before harvest
7) Place a blank Packard GF/B filter plate into the vacuum filter device (Packard plate harvester) and aspirate 200 mL water through to wet the system.
8) Take out the blank and put in the Packard GF/B filter plate.
9) Aspirate the reaction through the filter plate.
10) Wash: 200 mL each wash; 1× with 2M NaCl; 1× with 2M NaCl/1% H$_3$PO$_4$
11) Allow filter plate to dry 15 minutes.
12) Put TopSeal-A adhesive on top of filter plate.
13) Run filter plate in Top Count
  Settings: Data mode: CPM
  Radio nuclide: Manual SPA:P33
  Scintillator: Liq/plast
  Energy Range: Low IC$_{50}$ Determinations:

Dose-response curves were plotted from inhibition data generated, each in duplicate, from 8 point serial dilutions of inhibitory compounds, Concentration of compound was plotted against % kinase activity, calculated by CPM of treated samples divided by CPM of untreated samples. To generate IC$_{50}$ values, the dose-response curves were then fitted to a standard sigmoidal curve and IC$_{50}$ values were derived by nonlinear regression analysis.

Selected Thiazole Derivatives of the present invention were tested using this assay and provided IC$_{50}$ values ranging from about 1 nM to about 5500 nM.

CDK2 Kinase Assay

Baculovirus Constructions:

Cyclin E was cloned into pVL1393 (Pharmingen, La Jolla, Calif.) by PCR, with the addition of 5 histidine residues at the amino-terminal end to allow purification on nickel resin. The expressed protein was approximately 45 kDa. CDK2 was cloned into pVL1393 by PCR, with the addition of a haemaglutinin epitope tag at the carboxy-terminal end (YDVPD-YAS SEQ ID NO: 2). The expressed protein was approximately 34 kDa in size.

Enzyme Production:

Recombinant baculoviruses expressing cyclin E and CDK2 were co-infected into SF9 cells at an equal multiplicity of infection (MOI=5), for 48 hrs. Cells were harvested by centrifugation at 1000 RPM for 10 minutes, then pellets lysed on ice for 30 minutes in five times the pellet volume of lysis buffer containing 50 mM Tris pH 8.0, 150 mM NaCl, 1% NP40, 1 mM DTT and protease inhibitors (Roche Diagnostics GmbH, Mannheim, Germany). Lysates were spun down at 15000 RPM for 10 minutes and the supernatant retained. 5 mL of nickel beads (for one liter of SF9 cells) were washed three times in lysis buffer (Qiagen GmbH, Germany). Imidazole was added to the baculovirus supernatant to a final concentration of 20 mM, then incubated with the nickel beads for 45 minutes at 4° C. Proteins were eluted with lysis buffer containing 250 mM imidazole. Eluate was dialyzed about 15 hours in 2 liters of kinase buffer containing 50 mM Tris pH 8.0, 1 mM DTT, 10 mM $MgCl_2$, 100 μM sodium orthovanadate and 20% glycerol. Enzyme was stored in aliquots at −70° C.

In Vitro Cyclin E/CDK2 Kinase Assays

Cyclin E/CDK2 kinase assays can be performed as described below in low protein binding 96-well plates (Corning Inc, Corning, N.Y.).

Enzyme is diluted to a final concentration of 50 μg/mL in kinase buffer containing 50 mM Tris pH 8.0, 10 mM $MgCl_2$, 1 mM DTT, and 0.1 mM sodium orthovanadate. The substrate used in these reactions is a biotinylated peptide derived from Histone H1 (from Amersham, UK). The substrate is thawed on ice and diluted to 2 μM in kinase buffer. Test compounds are diluted in 10% DMSO to desirable concentrations. For each kinase reaction, 20 μL of the 50 μg/mL enzyme solution (1 μg of enzyme) and 20 μl of the 2 μM substrate solution are mixed, then combined with 10 μL of diluted compound in each well for testing. The kinase reaction is initiated by addition of 50 μL of 2 μM ATP and 0.1 μCi of 33P-ATP (from Amersham, UK). The reaction is allowed to run for 1 hour at room temperature, then is stopped by adding 200 μL of stop buffer containing 0.1% Triton X-100, 1 mM ATP, 5 mM EDTA, and 5 mg/mL streptavidine coated SPA beads (from Amersham, UK) for 15 minutes. The SPA beads are then captured onto a 96-well GF/B filter plate (Packard/Perkin Elmer Life Sciences) using a Filtermate universal harvester (Packard/Perkin Elmer Life Sciences.), Non-specific signals are eliminated by washing the beads twice with 2M NaCl then twice with 2 M NaCl with 1% phosphoric acid. The radioactive signal can then be measured using, for example, a Top-Count 96 well liquid scintillation counter (from Packard/Perkin Elmer Life Sciences).

$IC_{50}$ Determinations:

Dose-response curves are plotted from inhibition data generated, each in duplicate, from 8 point serial dilutions of inhibitory compounds. Concentration of compound is plotted against % kinase activity, calculated by CPM of treated samples divided by CPM of untreated samples. To generate $IC_{50}$ values, the dose-response curves are then fitted to a standard sigmoidal curve and $IC_{50}$ values can be derived using nonlinear regression analysis.

Compounds of the present invention exhibit mTOR $IC_{50}$ values of about 1 nM to about 5500 nM, CHK1 $IC_{50}$ values of about 100 nM to about 55000 nM, and CDK2 $IC_{50}$ values of about 800 nM to about 30000 nM. In all cases, the compounds are much more selective for mTOR over CHK1 and CDK2.

The following table shows the activity data for an illustrative list of compounds of the invention.

| Example No. | Structures | mTOR Activity |
|---|---|---|
| 1 | [chemical structure] | ++ |
| 2 | [chemical structure] | ++ |
| 3 | [chemical structure] | +++ |
| 4 | [chemical structure] | + |

| Example No. | Structures | mTOR Activity |
|---|---|---|
| 5 | 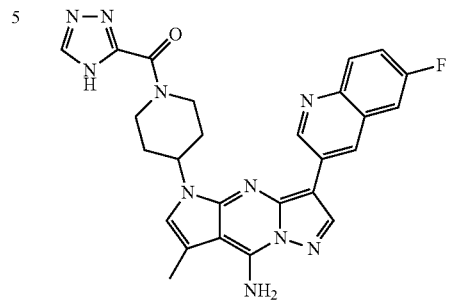 | + |
| 6 | 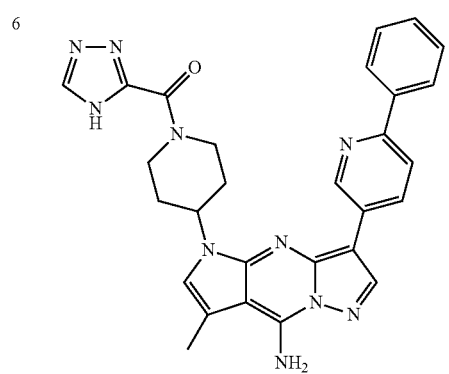 | ++ |
| 7 | 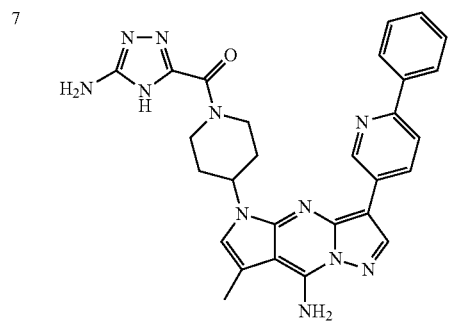 | ++ |
| 8 | 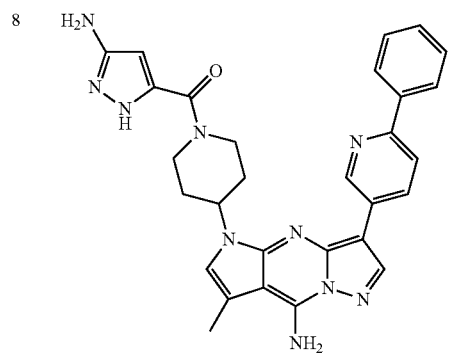 | ++ |
| Example No. | Structures | mTOR Activity |
|---|---|---|
| 9 | 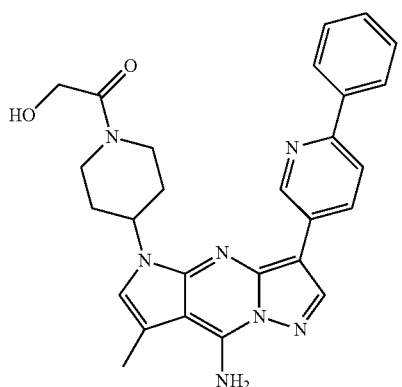 | + |
| 10 | 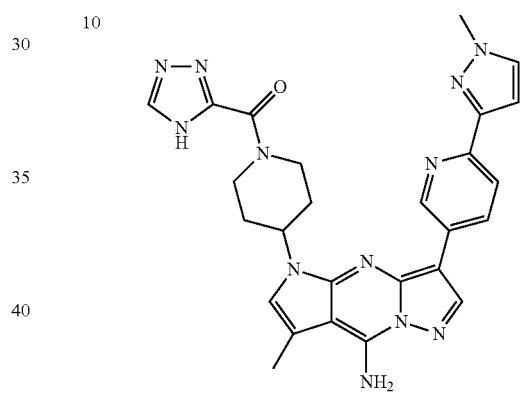 | + |
| 11 | | ++ |
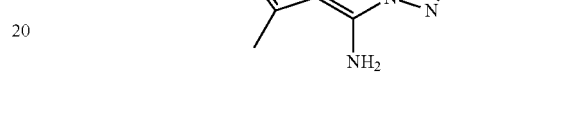
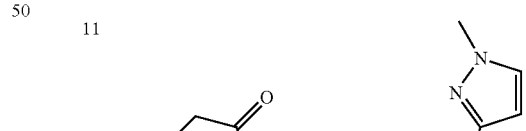
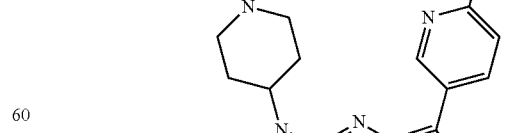
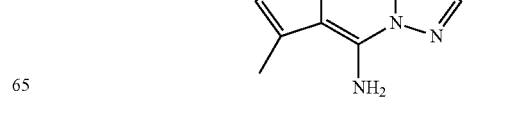

-continued

| Example No. | Structures | mTOR Activity |
|---|---|---|
| 12 | 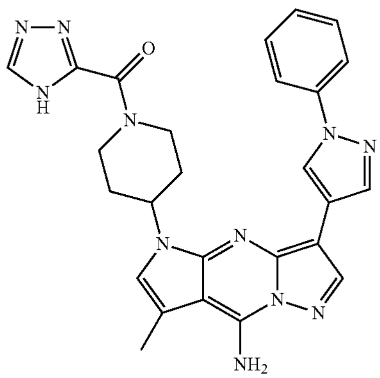 [SMILES: Cc1cn(C2CCN(C(=O)c3nnc[nH]3)CC2)c2nc3c(-c4cnn(-c5ccccc5)c4)cnn3c(N)c12] | ++ |
| 13 | 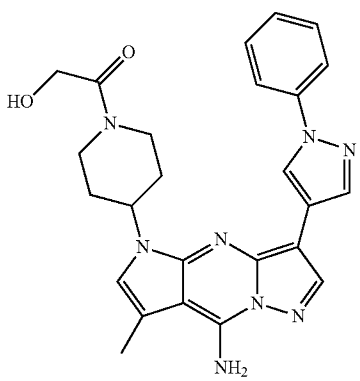 [SMILES: Cc1cn(C2CCN(C(=O)CO)CC2)c2nc3c(-c4cnn(-c5ccccc5)c4)cnn3c(N)c12] | + |
| 14 | 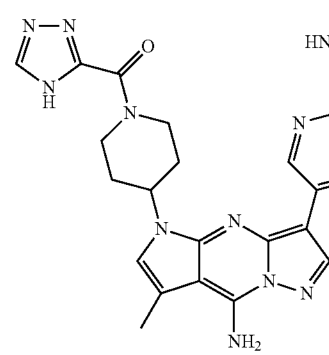 | + |
| 15 | 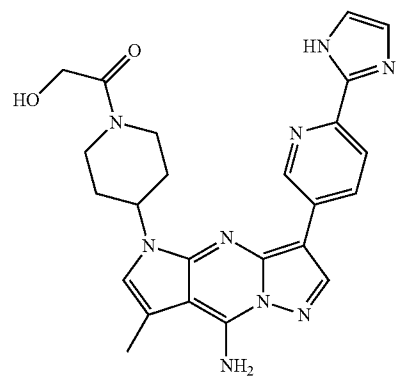 [SMILES: Cc1cn(C2CCN(C(=O)CO)CC2)c2nc3c(-c4ccc(-c5ncc[nH]5)nc4)cnn3c(N)c12] | + |

+++ IC50 >100 nM
++ IC50 = 10-100 nM
+ IC50 <10 nM

What is claimed is:

1. A compound of the formula:

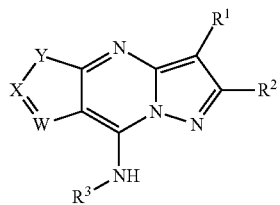

wherein the dotted line between W and X represents an optional double bond;

W is $CR^xR^y$;
X is $CR^xR^y$;
Y is $NR^5$;
$R^1$ is —$C(O)R^5$, $C_{2-6}$ alkenyl, $C_{2-6}$ alkynyl, $C_{3-8}$ cycloalkyl, $C_{3-8}$ cycloalkenyl, aryl, heteroaryl or heterocyclyl, wherein said alkyl, alkenyl, alkynyl, cycloalkyl, cycloalkenyl, aryl, heteroaryl and heterocyclyl groups are optionally substituted with one to three substituents independently selected from the group consisting of $R^4$, halo, cyano, $C_{1-6}$ alkyl, $C_{1-6}$ haloalkyl, $(CR^yR^z)_mOR^y$, $(CR^yR^z)_mNR^yR^z$, $C(O)R^y$, $C(O)OR^y$, $SO_mR^y$, $C(O)NR^yR^z$, $NR^yC(O)R^3$ and $NHR^4$;
$R^2$ is hydrogen, halo, cyano, $NR^yR^z$, $OR^y$, $C_{1-6}$ alkyl or $C_{1-6}$ haloalkyl;
$R^3$ is hydrogen, $NR^yR^z$, $(CR^yR^z)_mOR^y$, $C_{1-6}$ alkyl, $C_{2-6}$ alkenyl, $C_{2-6}$ alkynyl, $C_{3-8}$ cycloalkyl, $C_{3-8}$ cycloalkenyl, aryl, heteroaryl or heterocyclyl, wherein said cycloalkyl, cycloalkenyl, aryl, heteroaryl and heterocyclyl groups are optionally substituted with one to three substituents independently selected from the group consisting of halo, cyano, $C_{1-6}$ alkyl, $C_{1-6}$ haloalkyl and $OR^y$;
$R^4$ is $C_{3-8}$ cycloalkyl, $C_{3-8}$ cycloalkenyl, aryl, heteroaryl or heterocyclyl, wherein said cycloalkyl, cycloalkenyl, aryl, heteroaryl and heterocyclyl groups are optionally substituted with one to three substituents independently selected from the group consisting of halo, cyano, $C_{1-6}$ alkyl, $C_{1-6}$ haloalkyl, $(CR^yR^z)_mOR^y$, $O(C_{1-6}$ haloalkyl), $C(O)R^y$, $C(O)OR^y$, $SO_mR^y$ and $NR^yR^z$;
$R^5$ is hydrogen, aryl, heteroaryl, heterocyclyl or heterocyclyl($R^6$);
$R^6$ is not present, (C=O)$C_{1-6}$ alkyl, (C=O)aryl, (C=O)heteroaryl, (C=O)O($C_{1-6}$ alkyl)-$R^4$, wherein said alkyl and heteroaryl groups are optionally substituted with one to three substituents independently selected from the group consisting of halo, hydroxyl and $NR^yR^z$;
$R^x$ is hydrogen or $C_{1-6}$ alkyl;
$R^y$ is not present, hydrogen, $C_{1-6}$ alkyl or $C_{1-6}$ haloalkyl, wherein said alkyl group is optionally substituted with one to three hydroxyl;
$R^z$ is hydrogen, $C_{1-6}$ alkyl or $C_{1-6}$ haloalkyl, wherein said alkyl group is optionally substituted with one to three hydroxyl;
m is an integer from zero to two;
or a pharmaceutically acceptable salt thereof.

2. The compound of claim 1 wherein $R^2$ is hydrogen; or a pharmaceutically acceptable salt thereof.

3. The compound of claim 2 wherein $R^3$ is hydrogen; or a pharmaceutically acceptable salt thereof.

4. The compound of claim 3 wherein $R^1$ is heteroaryl wherein said heteroaryl is optionally substituted with one to three substituents independently selected from the group consisting of $R^4$, halo and $C_{1-6}$ alkyl; or a pharmaceutically acceptable salt thereof.

5. The compound of claim 4 wherein $R^1$ is pyridinyl or quinolinyl wherein said pyridinyl and quinolinyl groups are optionally substituted with one to three substituents independently selected from the group consisting of $R^4$, halo and $C_{1-6}$ alkyl; or a pharmaceutically acceptable salt thereof.

6. The compound of claim 4 wherein $R^4$ is aryl or heteroaryl, wherein said heteroaryl group is optionally substituted with $C_{1-6}$ alkyl; or a pharmaceutically acceptable salt thereof.

7. The compound of claim 1 that is selected from

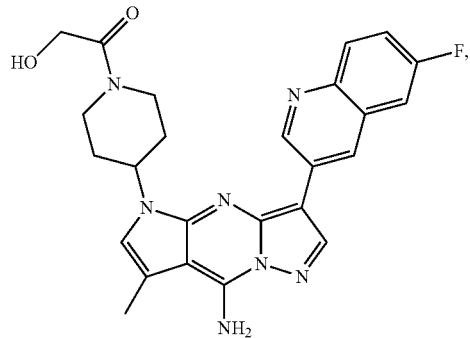

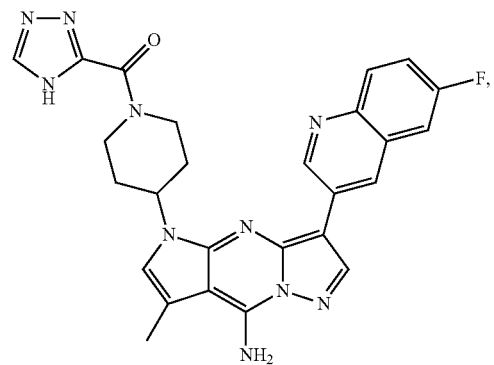

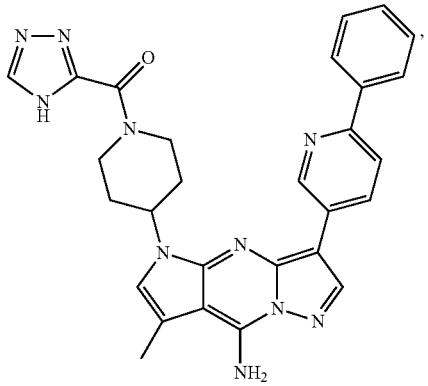

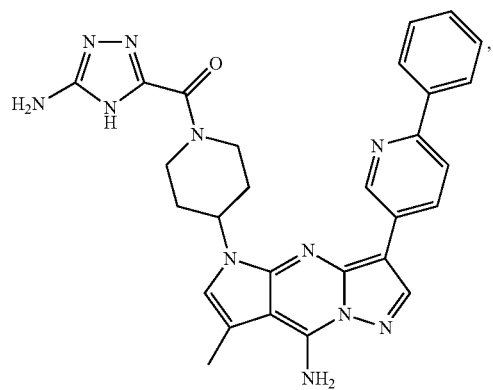
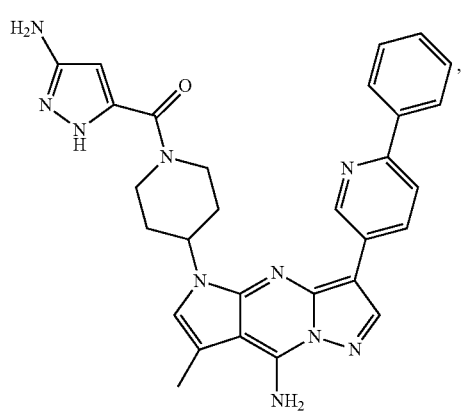
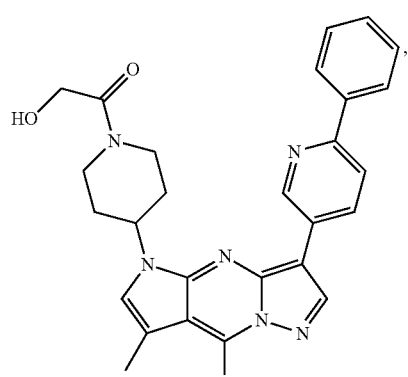
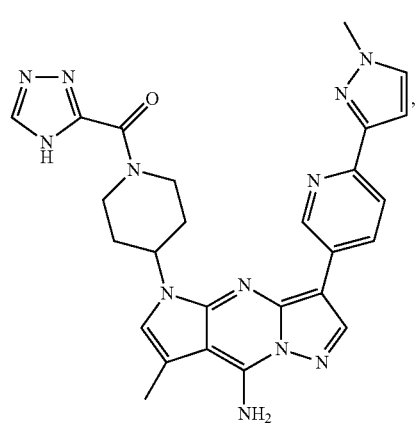
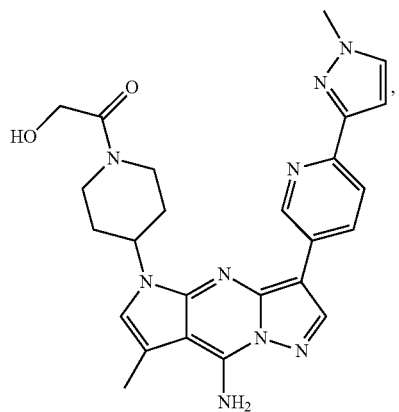
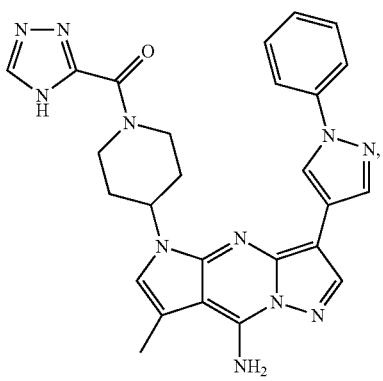
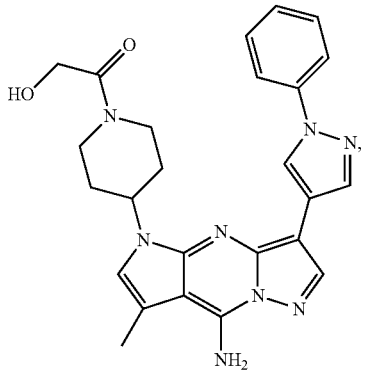
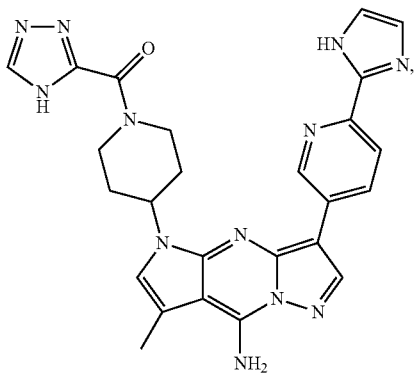

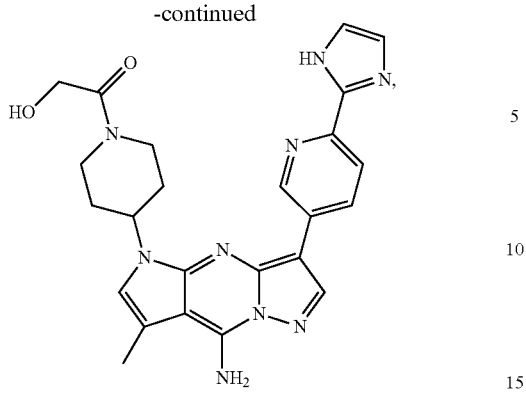
or a pharmaceutically acceptable salt thereof.
8. A pharmaceutical composition comprising a pharmaceutically effective amount of the compound according to claim 1, and a pharmaceutically acceptable carrier.

```
                          SEQUENCE LISTING

<160> NUMBER OF SEQ ID NOS: 2

<210> SEQ ID NO 1
<211> LENGTH: 18
<212> TYPE: PRT
<213> ORGANISM: Artificial Sequence
<220> FEATURE:
<223> OTHER INFORMATION: substrate

<400> SEQUENCE: 1

Arg Ser Gly Leu Tyr Arg Ser Pro Ser Met Pro Glu Asn Leu Asn Arg
1               5                   10                  15

Pro Arg

<210> SEQ ID NO 2
<211> LENGTH: 8
<212> TYPE: PRT
<213> ORGANISM: Artificial Sequence
<220> FEATURE:
<223> OTHER INFORMATION: epitope tag

<400> SEQUENCE: 2

Tyr Asp Val Pro Asp Tyr Ala Ser
1               5
```